(12) United States Patent
Burnett et al.

(10) Patent No.: US 10,398,824 B2
(45) Date of Patent: *Sep. 3, 2019

(54) DIALYSIS IMPLANT AND METHODS OF USE

(71) Applicant: SEQUANA MEDICAL NV, Zwijnaarde (BE)

(72) Inventors: Daniel R. Burnett, San Francisco, CA (US); Gregory W. Hall, Redwood City, CA (US)

(73) Assignee: Sequana Medical NV, Zwijnaarde (BE)

( * ) Notice: Subject to any disclaimer, the term of this patent is extended or adjusted under 35 U.S.C. 154(b) by 790 days.

This patent is subject to a terminal disclaimer.

(21) Appl. No.: 14/856,447

(22) Filed: Sep. 16, 2015

(65) Prior Publication Data

US 2016/0000984 A1 Jan. 7, 2016

Related U.S. Application Data

(63) Continuation of application No. 13/473,516, filed on May 16, 2012, now Pat. No. 9,138,523, which is a (Continued)

(51) Int. Cl.
*A61M 1/16* (2006.01)
*A61M 1/28* (2006.01)

(52) U.S. Cl.
CPC .......... *A61M 1/282* (2014.02); *A61M 1/1656* (2013.01); *A61M 1/1678* (2013.01); (Continued)

(58) Field of Classification Search
CPC ...... A61M 1/1678; A61M 1/28; A61M 1/282; A61M 1/285; A61M 1/1656; A61M 2205/04; A61M 2230/005
See application file for complete search history.

(56) References Cited

U.S. PATENT DOCUMENTS 3,540,451 A 11/1970 Zenman
3,575,158 A 4/1971 Summers
(Continued)

FOREIGN PATENT DOCUMENTS

CN 101485683 A 7/2009
CN 201930383 U 8/2011
(Continued)

OTHER PUBLICATIONS

Costanzo et al., "Early Ultrafiltration in Patients with Decompensated Heart Failure and Diuretic Resistance," J. Am. Coll. Cardiol., (2005), vol. 46(11):2047-2051.
(Continued)

*Primary Examiner* — Theodore J Stigell
(74) *Attorney, Agent, or Firm* — Foley & Lardner LLP; Christopher C. Bolten; Nicola A. Pisano

(57) ABSTRACT

A device and methods for treating renal failure are disclosed. One embodiment of the device is an implantable peritoneal dialysis device. When in use, the device can have a semi-permeable reservoir implanted in the peritoneal cavity. The reservoir can receive blood waste and drain through one or more conduits, via a pump, to the biological bladder. Solids and/or a solution benefiting dialysis can be pumped to the reservoir and/or implanted in the peritoneal cavity.

13 Claims, 27 Drawing Sheets

Related U.S. Application Data continuation of application No. 10/922,478, filed on Aug. 18, 2004, now Pat. No. 8,202,248.

(52) U.S. Cl.
CPC .............. *A61M 1/28* (2013.01); *A61M 1/285* (2013.01); *A61M 2205/04* (2013.01); *A61M 2230/005* (2013.01)

(56) References Cited

U.S. PATENT DOCUMENTS

| | | | |
|---|---|---|---|
| 3,654,932 A | 4/1972 | Newkirk et al. | |
| 3,810,259 A | 5/1974 | Summers | |
| 3,910,283 A | 10/1975 | Leveen | |
| 4,014,346 A * | 3/1977 | Brownlee | A61N 1/3787 |
| | | | 429/49 |
| 4,083,786 A | 4/1978 | Tsuda et al. | |
| 4,240,434 A | 12/1980 | Newkirk | |
| 4,261,341 A | 4/1981 | Hakim et al. | |
| 4,354,933 A | 10/1982 | Lester | |
| 4,416,657 A | 11/1983 | Berglund | |
| 4,419,094 A | 12/1983 | Patel | |
| 4,475,898 A | 10/1984 | Brodner et al. | |
| 4,475,899 A | 10/1984 | Muller | |
| 4,490,137 A | 12/1984 | Moukheibir | |
| 4,553,956 A | 11/1985 | Muller | |
| 4,610,625 A | 9/1986 | Bunn | |
| 4,610,658 A | 9/1986 | Buchwald et al. | |
| 4,615,691 A | 10/1986 | Hakim et al. | |
| 4,618,343 A | 10/1986 | Polaschegg | |
| 4,632,435 A | 12/1986 | Polyak | |
| 4,657,530 A | 4/1987 | Buchwald et al. | |
| 4,687,471 A | 8/1987 | Twardowski et al. | |
| 4,725,207 A | 2/1988 | Buchwald et al. | |
| 4,772,257 A | 9/1988 | Hakim et al. | |
| 4,779,614 A | 10/1988 | Moise | |
| 4,784,638 A | 11/1988 | Ghajar et al. | |
| 4,850,955 A | 7/1989 | Newkirk et al. | |
| 4,880,414 A | 11/1989 | Whipple | |
| 4,904,236 A | 2/1990 | Redmont et al. | |
| 4,963,129 A | 10/1990 | Rusch | |
| 4,963,133 A | 10/1990 | Whipple | |
| 5,011,472 A | 4/1991 | Aebischer et al. | |
| 5,021,048 A | 6/1991 | Buckholtz | |
| 5,037,385 A | 8/1991 | O'Byrne | |
| 5,057,075 A | 10/1991 | Moncrief et al. | |
| 5,071,408 A | 12/1991 | Ahmed et al. | |
| 5,078,688 A | 1/1992 | Lobodzinski et al. | |
| 5,147,281 A | 9/1992 | Thornton et al. | |
| 5,167,615 A | 12/1992 | East et al. | |
| 5,180,387 A | 1/1993 | Ghajar et al. | |
| 5,254,084 A | 10/1993 | Geary | |
| 5,356,386 A | 10/1994 | Goldberg et al. | |
| 5,385,541 A | 1/1995 | Kirsch et al. | |
| 5,387,188 A | 2/1995 | Watson | |
| 5,387,192 A | 2/1995 | Glantz et al. | |
| 5,391,143 A | 2/1995 | Kensey | |
| 5,395,350 A | 3/1995 | Summers | |
| 5,397,354 A | 3/1995 | Wilk et al. | |
| 5,472,323 A | 12/1995 | Hirabayashi et al. | |
| 5,474,683 A | 12/1995 | Bryant et al. | |
| 5,575,770 A | 11/1996 | Melsky et al. | |
| 5,589,197 A | 12/1996 | Shockley et al. | |
| 5,629,025 A | 5/1997 | Shockley et al. | |
| 5,631,025 A | 5/1997 | Shockley et al. | |
| 5,637,083 A | 6/1997 | Bertrand et al. | |
| 5,725,506 A | 3/1998 | Freeman et al. | |
| 5,830,172 A | 11/1998 | Leveen et al. | |
| 5,902,336 A * | 5/1999 | Mishkin | A61F 2/064 |
| | | | 604/27 |
| 5,944,684 A | 8/1999 | Roberts et al. | |
| 5,947,911 A | 9/1999 | Wong et al. | |
| 5,980,478 A | 11/1999 | Gorsuch et al. | |
| 5,989,207 A | 11/1999 | Hughes | |
| 6,007,511 A | 12/1999 | Prywes | |
| 6,017,355 A | 1/2000 | Hessel et al. | |
| D420,738 S | 2/2000 | Carter et al. | |
| 6,022,333 A | 2/2000 | Kensey | |
| 6,132,405 A | 10/2000 | Nilsson et al. | |
| 6,132,415 A | 10/2000 | Finch et al. | |
| 6,162,238 A | 12/2000 | Kaplan et al. | |
| 6,162,487 A | 12/2000 | Darouiche | |
| 6,193,684 B1 | 2/2001 | Burbank et al. | |
| 6,214,802 B1 | 4/2001 | Nakamura et al. | |
| 6,245,039 B1 | 6/2001 | Brugger et al. | |
| 6,248,726 B1 | 6/2001 | Alsop et al. | |
| 6,254,567 B1 | 7/2001 | Treu et al. | |
| 6,264,601 B1 | 7/2001 | Jassawalla et al. | |
| 6,264,625 B1 | 7/2001 | Rubenstein et al. | |
| 6,417,750 B1 | 7/2002 | Sohn | |
| 6,436,087 B1 | 8/2002 | Lewis et al. | |
| 6,533,733 B1 | 3/2003 | Ericson et al. | |
| 6,554,822 B1 | 4/2003 | Holschneider et al. | |
| 6,585,681 B2 | 7/2003 | Brugger et al. | |
| 6,613,095 B1 | 9/2003 | Levin | |
| 6,656,227 B2 | 12/2003 | Levin | |
| 6,689,085 B1 | 2/2004 | Rubenstein et al. | |
| 6,814,547 B2 | 11/2004 | Childers et al. | |
| 6,827,682 B2 | 12/2004 | Bugge et al. | |
| 6,845,267 B2 | 1/2005 | Harrison et al. | |
| 6,846,168 B2 | 1/2005 | Davis et al. | |
| 6,854,467 B2 | 2/2005 | Boekstegers | |
| 6,875,192 B1 | 4/2005 | Saul et al. | |
| 6,887,214 B1 | 5/2005 | Levin et al. | |
| 6,894,456 B2 | 5/2005 | Tsukamoto et al. | |
| 6,905,474 B2 | 6/2005 | Borgesen | |
| 6,911,014 B2 | 6/2005 | Wentling et al. | |
| 6,921,378 B2 | 7/2005 | O'Keefe et al. | |
| 6,926,691 B2 | 8/2005 | Miethke | |
| 6,939,111 B2 | 9/2005 | Huitt et al. | |
| 6,945,949 B2 | 9/2005 | Wilk | |
| 6,949,080 B2 | 9/2005 | Wolf et al. | |
| 6,953,481 B2 | 10/2005 | Phelps et al. | |
| 6,955,655 B2 | 10/2005 | Burbank et al. | |
| 6,960,179 B2 | 11/2005 | Gura | |
| 6,964,652 B2 | 11/2005 | Guiles et al. | |
| 6,974,445 B2 | 12/2005 | Stergiopulos | |
| 6,976,973 B1 | 12/2005 | Ruddell et al. | |
| 6,979,351 B2 | 12/2005 | Forsell et al. | |
| 6,981,964 B2 | 1/2006 | Rioux et al. | |
| 6,994,700 B2 | 2/2006 | Elkins et al. | |
| 7,011,095 B2 | 3/2006 | Wolf et al. | |
| 7,017,340 B2 | 3/2006 | Chicky | |
| 7,025,739 B2 | 4/2006 | Saul | |
| 7,025,742 B2 | 4/2006 | Rubenstein et al. | |
| 7,063,679 B2 | 6/2006 | Maguire et al. | |
| 7,169,303 B2 | 1/2007 | Sullivan et al. | |
| 7,195,608 B2 | 3/2007 | Burnett | |
| 7,311,690 B2 | 12/2007 | Burnett | |
| 7,335,179 B2 | 2/2008 | Burnett | |
| 7,621,886 B2 | 11/2009 | Burnett | |
| 7,670,332 B2 | 3/2010 | O'Keefe et al. | |
| 7,909,790 B2 | 3/2011 | Burnett | |
| 8,012,118 B2 | 9/2011 | Curtin et al. | |
| 8,202,248 B2 * | 6/2012 | Burnett | A61M 1/1678 |
| | | | 604/131 |
| 8,241,239 B2 | 8/2012 | Solomon et al. | |
| 8,394,048 B2 | 3/2013 | Burnett | |
| 8,398,577 B2 | 3/2013 | Burnett | |
| 8,517,973 B2 | 8/2013 | Burnett | |
| 8,585,635 B2 | 11/2013 | Degen et al. | |
| 8,641,659 B2 | 2/2014 | Soykan et al. | |
| 8,771,221 B2 | 7/2014 | Burnett | |
| 8,882,699 B2 | 11/2014 | Burnett | |
| 8,961,448 B2 | 2/2015 | Forsell | |
| 8,992,456 B1 | 3/2015 | Powell | |
| 9,039,652 B2 | 5/2015 | Degen et al. | |
| 9,138,523 B2 * | 9/2015 | Burnett | A61M 1/1678 |
| 9,144,660 B2 | 9/2015 | Degen | |
| 9,149,613 B2 | 10/2015 | Degen et al. | |
| D743,542 S | 11/2015 | Degen Thomas | |
| D743,543 S | 11/2015 | Degen Thomas | |
| 9,339,636 B1 | 5/2016 | Khan et al. | |
| 9,381,301 B2 | 7/2016 | Lattanzio et al. | |

(56) References Cited

U.S. PATENT DOCUMENTS

| | | |
|---|---|---|
| 9,421,347 B2 | 8/2016 | Burnett |
| 9,577,459 B2 | 2/2017 | Degen et al. |
| 9,675,327 B2 | 6/2017 | Johnson et al. |
| 9,913,968 B2 | 3/2018 | Burnett |
| 9,956,336 B2 | 5/2018 | Degen |
| 2002/0013545 A1 | 1/2002 | Soltanpour et al. |
| 2002/0022793 A1 | 2/2002 | Bertrand et al. |
| 2002/0123715 A1 | 9/2002 | Sorenson et al. |
| 2003/0114787 A1 | 6/2003 | Gura |
| 2003/0163079 A1 | 8/2003 | Burnett |
| 2003/0171710 A1 | 9/2003 | Bassuk et al. |
| 2003/0217962 A1 | 11/2003 | Childers et al. |
| 2003/0220606 A1 | 11/2003 | Busby et al. |
| 2004/0018228 A1 | 1/2004 | Fischell et al. |
| 2004/0049288 A1 | 3/2004 | Levin |
| 2004/0098113 A1 | 5/2004 | Forsell et al. |
| 2004/0126775 A1 | 7/2004 | Altieri et al. |
| 2004/0147871 A1 | 7/2004 | Burnett |
| 2005/0131340 A1 | 6/2005 | Sorenson et al. |
| 2005/0273034 A1 | 12/2005 | Burnett |
| 2006/0010014 A1 | 1/2006 | Brown |
| 2006/0024200 A1 | 2/2006 | Nishikiori et al. |
| 2006/0036208 A1 | 2/2006 | Burnett |
| 2006/0058731 A1 | 3/2006 | Burnett et al. |
| 2006/0094984 A1 | 5/2006 | Wood et al. |
| 2007/0055197 A1 | 3/2007 | Shakir |
| 2007/0106205 A1 | 5/2007 | Connell et al. |
| 2007/0228071 A1 | 10/2007 | Kamen et al. |
| 2007/0255345 A1 | 11/2007 | Krause |
| 2007/0299317 A1 | 12/2007 | Hoyme et al. |
| 2008/0108935 A1 | 5/2008 | Nyhart, Jr. |
| 2008/0154173 A1 | 6/2008 | Burnett |
| 2008/0214983 A1 | 9/2008 | Mauge et al. |
| 2008/0230450 A1 | 9/2008 | Burbank et al. |
| 2009/0069642 A1 | 3/2009 | Gao et al. |
| 2009/0171241 A1 | 7/2009 | Garcia et al. |
| 2009/0198174 A1 | 8/2009 | Childers et al. |
| 2009/0275924 A1 | 11/2009 | Lattanzio et al. |
| 2009/0318844 A1 | 12/2009 | Burnett |
| 2010/0010832 A1 | 1/2010 | Boute et al. |
| 2010/0114012 A1 | 5/2010 | Sandford et al. |
| 2010/0215375 A1 | 8/2010 | Reams |
| 2010/0249692 A1 | 9/2010 | Dacey et al. |
| 2010/0312163 A1 | 12/2010 | Forsell |
| 2010/0312164 A1 | 12/2010 | Forsell |
| 2011/0025261 A1 | 2/2011 | Bersenev |
| 2011/0034986 A1 | 2/2011 | Chou et al. |
| 2011/0184339 A1 | 7/2011 | Tan |
| 2011/0184340 A1 | 7/2011 | Tan et al. |
| 2012/0209085 A1 | 8/2012 | Degen et al. |
| 2012/0209165 A1 | 8/2012 | Degen et al. |
| 2013/0199998 A1 | 8/2013 | Kelly et al. |
| 2013/0211322 A1 | 8/2013 | Degen et al. |
| 2013/0289334 A1 | 10/2013 | Badstibner et al. |
| 2014/0012180 A1 | 1/2014 | Levin et al. |
| 2014/0066841 A1 | 3/2014 | Degen et al. |
| 2016/0000984 A1 | 1/2016 | Burnett et al. |
| 2016/0022971 A1 | 1/2016 | Degen et al. |
| 2016/0331947 A1 | 11/2016 | Burnett |
| 2017/0128654 A1 | 5/2017 | Feld |
| 2017/0281848 A1 | 10/2017 | Axelsson et al. |
| 2018/0056050 A1 | 3/2018 | Degen et al. |
| 2018/0060520 A1 | 3/2018 | Degen et al. |
| 2018/0344917 A1 | 12/2018 | Inhaber |

FOREIGN PATENT DOCUMENTS

| | | |
|---|---|---|
| EP | 0 366 389 A2 | 5/1990 |
| EP | 0 980 685 A2 | 2/2000 |
| EP | 1 362 605 A1 | 11/2003 |
| EP | 1 517 718 B1 | 3/2005 |
| EP | 1 539 294 B1 | 6/2005 |
| EP | 2 244 667 A1 | 11/2010 |
| EP | 2 676 638 B1 | 12/2013 |
| GB | 2 350 794 | 12/2000 |
| JP | H04-327857 | 11/1992 |
| JP | 2004-513681 | 5/2004 |
| JP | A2005-171892 | 6/2005 |
| WO | WO-97/41799 | 11/1997 |
| WO | WO-98/16171 | 4/1998 |
| WO | WO-99/34116 A1 | 7/1999 |
| WO | WO-02/07596 A1 | 1/2002 |
| WO | WO-03/072166 A1 | 9/2003 |
| WO | WO-2004/012806 A1 | 2/2004 |
| WO | WO-2004/105730 A1 | 12/2004 |
| WO | WO-2005/018708 A1 | 3/2005 |
| WO | WO-2006/023589 A2 | 3/2006 |
| WO | WO-2008/055248 A1 | 5/2008 |
| WO | WO-2009/096854 A1 | 8/2009 |
| WO | WO-2010/077851 A2 | 7/2010 |
| WO | WO-2012/112664 A1 | 8/2012 |
| WO | WO-2013/122580 A1 | 8/2013 |
| WO | WO-2013/166038 A2 | 11/2013 |
| WO | WO-2014/140277 A1 | 9/2014 |
| WO | WO-2015/108782 A1 | 7/2015 |
| WO | WO-2018/037359 A1 | 3/2018 |

OTHER PUBLICATIONS

Houlberg et al., "Terminal Right Heart Failure Due to Complex Congenital Cardiac Disease Successfully Managed by Home Peritoneal Drainage," Cardiol. Young, (2003), vol. 9(6):998-1005.

Ortiz et al., "Long-Term Automated Peritoneal Dialysis in Patients with Refractory Congestive Heart Failure," Advances in Peritoneal Dialysis, (2003), vol. 19:77-80.

PCT International Search Report dated Sep. 16, 2008 in PCT Application no. PCT/US2005/029305 (104476-0310).

Rosenblit et al., "Peritoneal-Urinary Drainage for Treatment of Refractory Ascites: a Pilot Study," J. Of Vascular & Interventional Radiology, (1998), vol. 9(6):998-1005.

Bellot, Pablo, et al., Automated low flow pump system for the treatment of refractory ascites: a multi-center safety and efficacy study, Journal of Hepatology, 58(5):922-927 (2013).

Fukuda, et al., Survivin, a cancer target with an emerging role in normal adult tissues, Mol. Cancer Ther., 5(5):1087-1098 (2006).

International Search Report & Written Opinion dated Mar. 18, 2013 in Intl PCT Appl. No. PCT/US2012/025188 (104476-0910).

International Search Report & Written Opinion dated Jan. 04, 2018 in Intl PCT Patent Appl. U.S. Appl. No. PCT/162017/055092 (104476-1410).

International Search Report and Written Opinion dated Apr. 16, 2015 in Intl PCT Patent Appl. No. PCT/US2015/010840 (104476-1610).

Partial International Search dated Dec. 8, 2017 in Intl PCT Patent Appl. No. PCT/1617/55093 (1044761710).

Medtronic Reveal LinqTM LNQ11, Insertable Cardiac Monitor, Clinician Manual, 98 pages (2015).

Rosenblit et al., "Peritoneal-urinary drainage for treatment of refractory ascites: a pilot study," J. Vascular & Interv. Radiology, 9(6):998-1005 (Nov./Dec. 1998).

Smyth, Chris,"Pump implant for cancer patients 'is a game-changer' for thousands", the Times, Health News, pg. 11, Jan. 18, 2013.

www.medtronic.com/us-en/patients/treatments-therapies/fainting-heart-monitor/reveal-linq-icm.html (May 2017) (Accessed Nov. 27, 2017).

Baxter Int , Baxter Healthcare Sa [Ch].

Potencia Medical Ag [Ch].

Milux Holding Sa [Lu].

Piolax Medical Devices Inc [Jp], Nat Cancer Ct [J P].

Gambro Lundia Ab [Se].

Nidus Medical Llc.

p. age () number(s), publisher, city and/or country where published. T6.

Doty, et al., Effect of Increased Renal Venous Pressure on Renal Function, J. Trauma., 47(6):1000-3 (1999).

Francois, et al., Peritoneal Dialysis for Chronic Congestive Heart Failure, Blood Purif., 40(1):45-52 (2015).

(56) References Cited

OTHER PUBLICATIONS

Hecking, et al., Sodium Setpoint and Sodium Gradient: Influence on Plasma Sodium Change and Weight Gain, Am J. Nephrol, 33(1):39-48 (2011).
International Search Report and Written Opinion dated Feb. 02, 2018 in Intl PCT Patent Appl. No. PCT/162017/055093 (104476-1710).
International Search Report and Written Opinion dated Aug. 24, 2018 in Intl PCT Patent Appl. U.S. Appl. No. PCT/162018/053587 (104476-1510).
Kenny, Intra-Abdominal Pressure and Renal Function: the Venous Side of the Road, PulmCCM, Critical Carer, Gi and Nutrition, Jul. 14, 2016, accessed on line on 3/27/17 at http://pulmccm.org/main/2016/critical-care-review/intra-abdominal-pressure-renal-function/.
McCAUSLAND, et al., Dialysate Sodium, Serum Sodium and Mortality in Maintenance Hemodialysis, 27(4):1613-1618 (2012).
Munoz Mendoza, et al., Dialysate sodium and sodium gradient in maintenance hemodialysis: a neglected sodium restriction approach? Nephrol Dial Transplant, 26(4):1281-1287 (2011).
Nakayama, et al., Clinical Effect of Low Na Concentration Dialysate (120mEq/L) for Capd Patients, Abstracts of the Xiii Annual Capd Conference, Peritoneal Dialysis International, vol. 13, Supplement 1,1993.
Puttagunta, et al., Peritoneal Dialysis for Heart Failure, Peritoneal Dialysis International, 35(6):645-649 (2015.
Ruhi, et al., Use of Peritoneal Ultrafiltration in the Elderly Refractory Congestive Heart Failure Patients, Int. Urol. And Nephrol., 44(3):963-969 (2012).
Zepeda-Orozco, et al., Dialysis Disequilibrium Syndrome, Pediatr. Nephrol, 27:2205-2211 (2012).

\* cited by examiner

DIALYSIS IMPLANT AND METHODS OF USE

CROSS-REFERENCE TO RELATED APPLICATIONS

This application is a continuation of U.S. patent application Ser. No. 13/473,516, filed May 16, 2012, now U.S. Pat. No. 9,138,523, which is a continuation of U.S. patent application Ser. No. 10/922,478, filed Aug. 18, 2004, now U.S. Pat. No. 8,202,248, the entire contents of each of which are incorporated herein by reference.

BACKGROUND OF THE INVENTION

1. Field of the Invention

The present invention relates to an implantable device for drug delivery and dialysis, particularly for peritoneal dialysis, and a method of using the system.

2. Description of the Related Art

Kidney failure is typically treated by dialysis until a kidney transplant or other treatment can replace the kidney function. Dialysis can be performed by hemodialysis or peritoneal dialysis (PD).

Hemodialysis treatment removes the blood from the body, often about 0.25 L (8.5 fl. oz.) at a time, and often from a blood vessel in the arm. The extra-corporeal blood is then passed through a semi-permeable membrane that removes the waste—including excess water—otherwise filtered by healthy kidneys, from the blood without the loss of desirable molecules. Hemodialysis patients typically receive three treatment sessions per week, with each session lasting 3 to 5 hours. Because proper maintenance of hemodialysis equipment (e.g., membranes, pumps) is critical, hemodialysis sessions are often performed at a treatment center.

PD treatment introduces a dialysis solution to the peritoneal cavity. The blood is naturally filtered through the organ membranes in the peritoneum. Blood waste naturally passes through the organ membranes in the peritoneal cavity. The waste is drawn into the peritoneal cavity by the osmotic pressure gradient created by the properly-formulated dialysis solution. After a few hours, the dialysis solution, loaded with waste, can be removed. A patient can perform the "exchanges" of dialysis solution at home, but must drain an extra-corporeal bag of dialysis solution into the peritoneal cavity, and then drain their own peritoneal cavity into an extra-corporeal bag—all through a trans-peritoneum catheter. Patients also usually undergo four to six exchanges a day.

PD is widely considered to be a more effective treatment for removing waste from the blood, but patients often prefer the relative infrequency and convenience of hemodialysis. Most patients also prefer not to receive the large quantity and depth of the punctures associated with PD.

U.S. Pat. No. 5,037,385 to O'Byrne discloses an implantable peritoneal dialysis system. The system includes an implanted trans-peritoneum catheter. The trans-peritoneal catheter terminates outside the peritoneal cavity at a subcutaneous self-sealing terminal structure and terminates inside the peritoneal cavity at an open end. Dialysis solution can be introduced directly into the subcutaneous self-sealing terminal structure. The solution then flows into the peritoneal cavity. The system also includes an implanted catheter that drains the peritoneal cavity into the bladder via a pump.

The system disclosed by O'Byrne may reduce the number of times the patient must drain their peritoneal cavity and may reduce the depth of the punctures needed to introduce dialysis solution to the peritoneal cavity. The system disclosed by O'Byrne, however, fails to increases the number of painful punctures needed to introduce the dialysis solution, fails to incorporate safeguards against pathologically high pressures in the urinary bladder or pathologically low levels of peritoneal fluid, fails to incorporate control mechanisms required for effective dialysis without dehydration, and fails to prevent loss of peritoneal proteins with extended use.

A need therefore exists for methods and devices for performing more convenient and painless PD. There exists a need to reduce the frequency of punctures patients receive during PD treatment. There also exists a need to reduce the depth of punctures during PD therapy. Furthermore, there exists a need to fulfill the above needs without negatively affecting the quality of blood waste removal.

BRIEF SUMMARY OF THE INVENTION

An implantable dialysis device is disclosed. In one embodiment of the implantable dialysis, the device has two components: an implantable peritoneourinary pump system and an implantable dialysate infusion system.

The implantable peritoneourinary pump system can have a first discharge conduit for the withdrawal of peritoneal fluid from the peritoneal cavity. The implantable peritoneourinary pump system can have a peritoneourinary pump. The implantable peritoneourinary pump system can have a second discharge conduit. The second discharge (i.e., exit) conduit can shunt the fluid into the bladder. The implantable peritoneourinary pump system can have peritoneal and urinary pressure sensors. The implantable peritoneourinary pump system can have a magnetically coupled pump powering or recharging mechanism.

The first discharge conduit can be in fluid communication with the peritoneal cavity and the peritoneourinary pump. The first discharge conduit can have one or more perforations. The perforations can allow for the influx of the peritoneal fluid. The first discharge conduit can have a semi-permeable membrane or reservoir. The membrane or reservoir can restrict the flow of certain components of the peritoneal fluid based on size and/or charge.

The peritoneourinary pump can be attached to the first and/or second conduits. The peritoneourinary pump can be programmable and/or controllable via an external signal generator. The peritoneourinary pump can be controlled as a function of time. The peritoneourinary pump can be controlled through negative and/or positive feedback loops, for example, using input from the pressure sensors.

The second discharge conduit can be in fluid communication with the peritoneourinary pump and the urinary bladder. The second discharge conduit can be fixedly attached to the bladder wall. The second discharge conduit can be coated, for example, to prevent encrustation.

The peritoneal and urinary pressure sensors can be loose in the peritoneal cavity and bladder, respectively, for example by being tethered but free-floating. The peritoneal and urinary pressure sensors can be incorporated into the first and second discharge conduits, respectively. The pressure sensors can be incorporated into the peritoneourinary pump housing. The peritoneal and urinary pressure sensors control the peritoneourinary pump in order to prevent excessive bladder pressure or abnormally low or high peritoneal pressure. The implantable dialysis device can also have moisture, protein, strain (e.g., in the bladder wall), nerve sensors (e.g., to detect nerve signals in the bladder, for example, to detect fullness), or combinations thereof.

The magnetically coupled pump powering mechanism can be used to directly drive the peritoneourinary pump by the transdermally application of magnetic forces and/or to inductively recharge the internal battery. In one embodiment, for example when the peritoneourinary pump is directly driven by magnetic forces, the first discharge conduit can pass from the subcutaneous space into the peritoneal cavity. The peritoneourinary pump can reside in the subcutaneous space. The second discharge conduit can pass from the subcutaneous space into the bladder. The subcutaneous location of the peritoneourinary pump can increase the applied strength of magnetic forces used to drive the peritoneourinary pump.

In a second embodiment, for example when the internal battery is inductively recharged, the implantable peritoneourinary pump system can be located anywhere in the peritoneal, urinary or subcutaneous space. The inductive recharging coil can be located in close proximity to the skin, for example, to increase the effectiveness of battery recharging.

When activated, the implantable peritoneourinary pump system can transfer peritoneal fluid into the bladder via the first discharge conduit, the peritoneourinary pump and the second discharge conduit. Peritoneal fluid transfer, for example through control of the peritoneourinary pump and/or valves, can be internally controlled via negative or positive feedback from pressure sensors and/or externally activated, for example, by a transdermal signal.

The implantable dialysate infusion system can elute concentrated dialysate, other osmotic agents, or other therapeutic and/or diagnostic agents, or combinations thereof, into the peritoneal cavity. The eluting can be performed chronically. The implantable dialysate infusion system can have a reservoir. The implantable dialysate infusion system can have a first transfer conduit. The implantable dialysate infusion system can have an infusion pump. The infusion pump and the peritoneourinary pump can be the same pump. The infusion pump and the peritoneourinary pump can be separate pumps. The implantable dialysate infusion system can have a second transfer conduit. The implantable dialysate infusion system can have a filling port.

The reservoir can be in fluid communication with the first transfer conduit and the filling port. The reservoir can be made, in part or whole, from as impermeable material. The impermeable material can prevent or minimize undesired leakage of dialysate into the peritoneal cavity. The implanted location of the reservoir can allow for the accommodation of large volumes of concentrated solute inside the reservoir. The reservoir can be located within the peritoneal cavity.

The first transfer conduit can be in fluid communication with the reservoir and the infusion pump. The first transfer conduit can be absent from the implantable dialysate infusion system, for example if the infusion pump is incorporated into the reservoir.

The infusion pump can be attached to the first and/or second transfer conduits. The infusion pump can be incorporated into the implantable peritoneourinary pump system. The infusion pump can be programmable and/or controllable via an external signal generator. The infusion pump can be controlled through either negative or positive feedback loops using the pressure sensors of the implantable peritoneourinary pump system. The infusion pump can be driven by methods similar to methods described supra for powering the pertioneourinary pump, for example, the infusion pump can be externally powered or rechargeable. The infusion pump can be activated and deactivated in conjunction with the implantable peritoneourinary pump system.

The second conduit can be in fluid communication with the infusion pump and the peritoneal cavity. The second conduit, with one or more perforations, can function as the first conduit of the implantable peritoneourinary pump system component of the device. The second conduit can terminate in a mixing chamber. The mixing chamber can dilute the concentrated or solid dialysate with the peritoneal fluid, for example, prior to discharge into the peritoneal cavity. Diluting and/or mixing the concentrated to solid dialysate with the peritoneal fluid can prevent local reaction, for example a hyperosmotic reaction, to the mixed fluid.

The filling port can be in fluid communication with the reservoir. The filling port can be implanted in a position providing minimally invasive or percutaneous access to the filling port. The filling port can have a self-sealing puncture membrane. The filling port can have a locating mechanism, for example, a magnetic field or another signal generating mechanism. The filling port can be locatable via palpation.

When activated, the implantable dialysate infusion system can transfer concentrated or solid dialysate from the reservoir into the peritoneal cavity, or mixing chamber, via the first conduit, the infusion pump and the second conduit. The implantable dialysate infusion system can have slow-release formulation of concentrated dialysate in the form of a dialysate solid or concentrated solute.

A method of using the implantable dialysis device in an animal having a peritoneal cavity and a bladder is disclosed. The method can include pumping dialysate, or other osmotic or other agent, from the reservoir into the peritoneal cavity. The method can include pumping some or all of the contents of the peritoneal cavity into the urinary bladder for evacuation, for example, after a time-delay from the introduction of additional agents into the peritoneal cavity. The method can include the percutaneous refilling of the reservoir. The method can include the use of timers and pressure sensors to automatically administer peritoneal dialysis. The method can minimize conscious patient interaction, for example, only requiring conscious patient interaction for the refilling of the reservoir and the recharging or activating of the pumps.

The implantable dialysate infusion system can be used to administer any agent such as a drug, diagnostic, or therapeutic, for example, when large volumes of the agent are to be administered. Due to the implantable dialysate infusion system's rechargeable nature, the implantable dialysate infusion system's ability to be refilled and its large volume peritoneal reservoir, large amounts of drug or therapeutic could be administered intravenously, subcutaneously or intraperitoneally over extended periods of time with only infrequent puncture for refilling of the reservoir.

DETAILED DESCRIPTION

Figure 1:
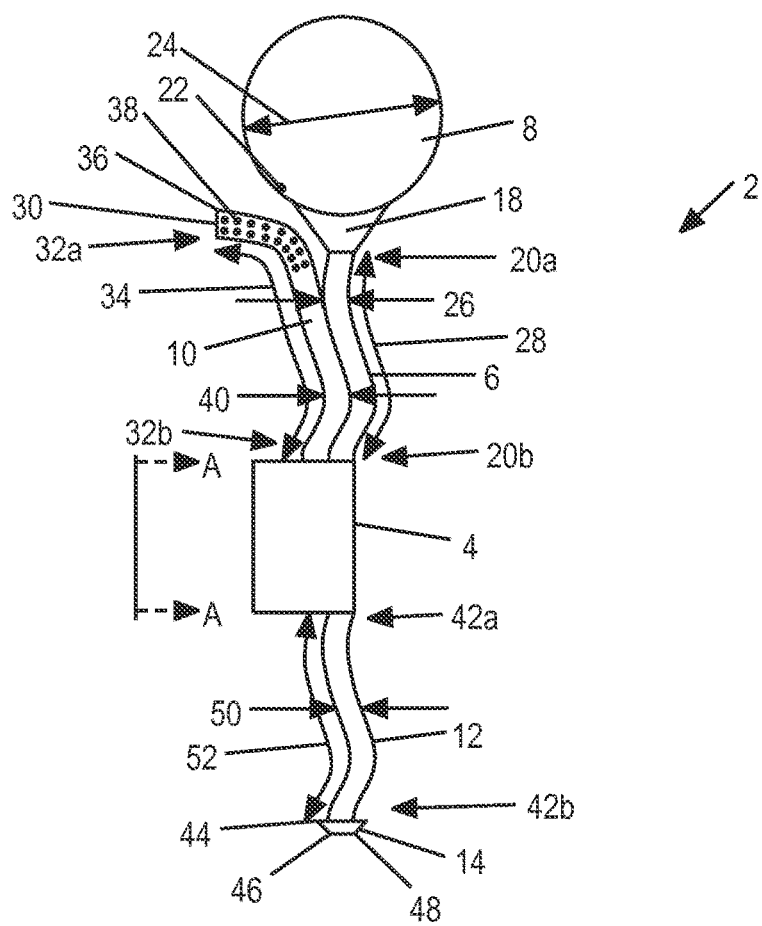
FIG. 1 illustrates an embodiment of the implantable dialysis device.

FIG. 1 illustrates an implantable dialysis device 2. The implantable dialysis device 2 can have a distributor 4. The distributor 4 can be configured to receive and distribute a dialysate and/or any other fluid or fluids, for example a solution of therapeutic and or diagnostic agents. The dialysate can be received by the distributor 4 and initially distributed through a reservoir conduit 6 to a reservoir 8. At a later time, the distributor 4 can withdraw the dialysate from the reservoir 8 and distribute the dialysate through a discharge conduit 10 to a peritoneal cavity (shown infra). At a later time, the distributor 4 can withdraw the dialysate and other waste fluids and solids from the peritoneal cavity through the discharge conduit 10. The distributor 4 can then distribute the withdrawn dialysate and waste fluid and solids through the exit conduit 12 and out an exit 14 to a bladder (shown infra).

The distributor 4 can be attached to a reservoir conduit 6. The reservoir conduit 6 can be attached to the reservoir 8. A reservoir connector 18 can attach the reservoir conduit 6 to the reservoir 8. The reservoir 8 can be in fluid communication with a reservoir conduit first end 20a. The reservoir connector 18 can reinforce the attachment between the reservoir 8 and the reservoir conduit first end 20a.

The reservoir 8 can be a substantially or completely impermeable, leak-proof container for indefinite storage of therapeutic and/or diagnostic fluids and/or solids. The reservoir 8 can be hollow. A reservoir sensor 22, such as a reservoir pressure sensor, reservoir pH sensor, reservoir temperature sensor, reservoir electrolyte sensor, reservoir analyte sensor, or combinations thereof, can be attached to the inside of the reservoir 8.

The reservoir 8 can be substantially spherical, circular, cylindrical, tubular, or have a shape similar to a partially flattened sphere. The reservoir 8 can be shaped to fit in the negative space around organs, for example in the cul-de-sac of the peritoneal cavity. The reservoir 8 can be made from at least two pieces of material. The pieces of material can be joined at the perimeters of the pieces of material. The pieces of material can be substantially circular.

The reservoir 8 can have a reservoir diameter 24. The reservoir diameter 24 can be from about 2 cm (0.8 in.) to about 20 cm (8 in.), more narrowly from about 4 cm (2 in.) to about 10 cm (4 in.), for example about 2 cm (0.8 in.), about 4 cm (2 in.), about 10 cm (4 in.), or about 20 cm (8 in.). The reservoir 8 can have a reservoir volume. The reservoir volume can be about 10 mL (0.6 in.$^3$) to about 3000 mL (200 in.$^3$), more narrowly from about 200 mL (10 in.$^3$) to about 2000 mL (100 in.$^3$), for example about 1500 mL (92 in.$^3$). The reservoir volume can depend on the potency (e.g., solute concentration) of the reservoir contents used with the reservoir 8.

The reservoir 8 can be substantially impermeable, for example the outer surface of the reservoir 8 can be made from a nonporous membrane or a membrane with sufficiently small pores to minimize or prevent flow across the surface of the reservoir 8.

The pore size can be dependent on the particle size of an agent (e.g., osmotic agent, dialysate) dispensed into the surrounding body cavity and/or tissue. The pore size can prevent leakage, for example, of particles with a molecular weight (MW) from about 50 to about 5000, more narrowly a MW less than about 800, yet more narrowly a MW from about 50 to about 100. The pores can be configured to exclude, for example, sugars and dialysates (e.g., with a MW of about 800), synthetic osmotic agents (e.g., a MW of less than or equal to about 5000), glucose (e.g., about 2.27% solution, MW of about 180.16), maltose, such as maltose disaccharide (e.g., about 4.32% solution, MW of about 342.30), maltotriose, such as maltotriose trisaccharide (e.g., about 6.36% solution, MW of about 504.44), and maltopentaose, such as maltopentaose pentasaccharide (e.g., about 10.4% solution, MW of about 828.72), any other osmotically active material, and combinations thereof.

The reservoir 8 can have pores having diameters substantially smaller than about 500 μm (19.7 mil), yet more narrowly from about 5 μm (0.2 mil) to about 200 μm (7.87 mil). ("Substantially smaller" can be having about 95% or more of the pores being smaller.) The reservoir 8 can have an average pore diameter from about 5 μm (0.2 mil) to about 500 μm (1.97 mil), for example about 10 μm (0.39 mil). The reservoir 8 can be made from any of the materials disclosed infra for all elements of the implantable dialysis device 2. The reservoir 8 can be made from a biocompatible impermeable membrane. The reservoir 8 can be made from, for example polymers, such as polyacrylonitrile (PAN), polysulfone (PS), polyethersulfone, poluethylene, polymethylmethacrylate (PMMA), polytetrafluoroethylene (PTFE) (e.g., TEFLON®, E. I. Du Pont de Nemours and Company, Wilmington, Del.), expanded PTFE (ePTFE) (e.g., GORE-TEX® from W.L. Gore & Associates, Inc., Newark, Del.), polyester (e.g., DACRON® from E. I. Du Pont de Nemours and Company, Wilmington, Del.), polypropylene, polyether ether ketone (PEEK), Nylon, polyether-block co-polyamide polymers (e.g., PEBAX® from ATOFINA, Paris, France), polyurethanes such as aliphatic polyether polyurethanes (e.g., TECOFLEX® from Thermedics Polymer Products, Wilmington, Mass.), polyvinyl chloride (PVC), thermoplastic, fluorinated ethylene propylene (FEP), cellulose (e.g., VISKING®, SERVAPOR®, MEMBRA-CEL®, or SPECTRA/POR® 1, 3 and 6 Dialysis Tubing from SERVA Electrophoresis GmbH of Heidelberg, Germany; Cupro-phane PT-150 from Enka-Glanstoff of Germany) such as a seamless regenerated cellulose and/or cellulose acetate (CA), extruded collagen, silicone, a metal, such as single or multiple stainless steel alloys, nickel titanium alloys (e.g., Nitinol), cobalt-chrome alloys (e.g., ELGILOY®; CON-ICHROME®), molybdenum alloys (e.g., molybdenum TZM alloy), tungsten-rhenium alloys, or combinations of any of the above.

The reservoir 8, as well as other elements in contact with the stored fluids, for example the elements from a filling port to the reservoir 8 and from the reservoir 8 to the distributor 4, can be made from strong and/or redundant materials having a thickness and construction such that the material can remain intact without leaking or becoming substantially permeable during conditions of extreme acceleration, for example in a halting car accident at about 89 km/h (55 miler per hour) producing, for example, an acceleration of about 991.5 m/s$^2$ (3,253 f/s$^2$).

The reservoir 8 can be made from a multi-layer and/or fiber-reinforced material. The reservoir 8 can be made from strong and redundant materials. The reservoir 8 can be made from a flexible or rigid material.

The reservoir conduit 6 can be configured to enable the fluid communication of dialysate or other fluid between the distributor 4 and the reservoir 8. The reservoir 8 can be fixedly, removable and/or rotatable attached, directly or indirectly, to the reservoir conduit first end 20a. The reservoir 8 can be in fluid communication with the reservoir conduit first end 20a. The distributor 4 can be attached to a reservoir conduit second end 20b. The distributor 4 can be in fluid communication with the reservoir conduit second end 20b.

The reservoir conduit 6 can be flexible or rigid. The reservoir conduit 6 can be deformable or resilient. The reservoir conduit 6 can be substantially impermeable.

The reservoir conduit 6 can have a reservoir conduit diameter 26 and a reservoir conduit length 28. The reservoir conduit diameter 26 can be from about 1 mm (0.04 in.) to about 10 mm (0.4 in.), more narrowly from about 2 mm (0.08 in.), to about 5 mm (0.2 in.), for example about 1 mm (0.04 in.), about 2 mm (0.08 in.), about 5 mm (0.2 in.), or about 10 mm (0.4 in.). The reservoir conduit length 28 can be from about 0 cm (0 in.) to about 50 cm (20 in.), more narrowly from about 5 cm (2 in.) to about 20 cm (8 in.), for example about 5 cm (2 in.), about 10 cm (4 in.), about 20 cm (8 in), or about 50 cm (20 in.).

The discharge conduit 10 can be configured to enable fluid communication of dialysate, waste liquids and solids, and/or other fluid between the distributor 4 and the peritoneal cavity. The peritoneal cavity can be in fluid communication with a discharge conduit first port 30 at a discharge conduit first end 32a. The distributor 4 can be attached to a discharge conduit second end 32b. The distributor 4 can be in fluid communication with the discharge conduit second end 32b.

The discharge conduit 10 can be substantially impermeable, permeable, semi-permeable or combinations thereof. The discharge conduit first port 30 can have an opening, and/or a permeable, and/or a semi-permeable surface. The discharge conduit 10 can have multiple (not shown) discharge conduit first ports 30 that can be at the discharge conduit first end 32a and/or along a discharge conduit length 34. The discharge conduit first port 30 can be configured to minimize and/or prevent fluid communication of proteins, for example by size or charge exclusion (e.g., as described in detail supra for the reservoir and infra for the transfer element and barriers). A peritoneal cavity sensor 36, such as a peritoneal cavity pressure sensor, peritoneal cavity pH sensor, peritoneal cavity temperature sensor, peritoneal cavity electrolyte sensor, peritoneal cavity analyte sensor, or combinations thereof, can be attacked to the discharge conduit 10, for example on or adjacent to the discharge conduit first port 30.

The discharge conduit 10 can have one or more perforations 38 along part or all of the discharge conduit length 34. The perforations 38 can be along the discharge conduit first end 32a and/or along the discharge conduit second end 32b. The perforations 38 can be configured to allow the fluid communication of the dialysate or other fluids. The perforations 38 can be configured to maximize and/or prevent fluid communication of proteins for example by size or charge exclusion (e.g., as described herein). The perforations 38 can be configured to minimize and/or prevent fluid communication of dialysate solute.

The discharge conduit 10 can be flexible or rigid. The discharge conduit 10 can be deformable or resilient. The discharge conduit 10 can have a discharge conduit diameter 40 and the discharge conduit length 34. The discharge conduit diameter 40 can be from about 1 mm (0.04 in.) to about 10 mm (0.4 in.), more narrowly from about 2 mm (0.08 in.) to about 5 mm (0.2 in.), for example about 1 mm (0.04 in.), about 2 mm (0.08 in.), about 5 mm (0.2 in.), or about 10 mm (0.4 in.). The discharge conduit length 34 can be from about 0 cm (0 in.) to about 50 cm (20 in.), more narrowly from about 5 cm (2 in.) to about 20 cm (8 in.), for example about 5 cm (2 in.), about 10 cm (4 in.), about 20 cm (8 in), or about 50 cm (20 in.). The discharge conduit 10 can be shaped to fit in the negative space around one or more organs within the peritoneal cavity. The discharge conduit 10 can permit the inflow of bodily fluids required to mix with dialysate fluid (e.g., in concentrated form) or solid dialysate material prior to transfer into the peritoneal cavity.

The outer surface of the reservoir conduit 6 can be attached to the outer surface of the discharge conduit 10 along the entire, part, or none of the reservoir conduit length 28 and the discharge conduit length 34. The reservoir conduit 6 and the discharge conduit 10 can share a common outer conduit (not shown) along the entire or part of the reservoir conduit length 28 and the discharge conduit length 34. The common outer conduit can be distinct or integral with the reservoir conduit 6 and/or the discharge conduit 10.

The exit conduit 12 can be configured to enable the fluid communication of dialysate or other fluid between the distributor 4 and the bladder. The distributor 4 can be fixedly, removably and/or rotatably attached, directly or indirectly, to an exit conduit first end 42a. The distributor 4 can be in fluid communication with the second conduit first end 42a. The bladder (shown infra) can be attached to an exit conduit second end 42b, for example by fixedly attaching an anchor 44 at the exit conduit second end 42b against a wall of the bladder. For example, the anchor 44 can have a flange that can form a one-way interference fit with the wall of the bladder. The bladder, for example via an exit port 46, can be in fluid communication with the exit conduit second end 42b. A bladder sensor 48, such as a bladder pressure sensor, bladder pH sensor, bladder temperature sensor, bladder electrolyte sensor, bladder analyte sensor, or combinations thereof, can be attached to the exit conduit 12, for example on or adjacent to the exit port 46.

The exit conduit 12 can be substantially impermeable (e.g., outside the bladder) and/or semi-permeable (e.g., inside the bladder) and/or permeable (e.g., inside the bladder). The exit conduit 12 can be flexible or rigid. The exit conduit 12 can be deformable or resilient.

The exit conduit 12 can have an exit conduit diameter 50 and an exit conduit length 52. The exit conduit diameter 50 can be from about 1 mm (0.04 in.) to about 10 mm (0.4 in.), more narrowly from about 2 mm (0.08 in.) to about 5 mm (0.2 in.), for example about 1 mm (0.04 in.), about 2 mm (0.08 in.), about 5 mm (0.2 in.), or about 10 mm (0.4 in.). The exit conduit length 52 can be from about 0 cm (0 in.) to about 50 cm (20 in.), more narrowly from about 5 cm (2 in.) to about 20 cm (8 in.), for example about 5 cm (2 in.), about 10 cm (4 in.), about 20 cm (8 in.), or about 50 cm (20 in.).

The exit conduit 12 can be distinct from the reservoir conduit 6 and/or the discharge conduit 10. The exit conduit 12 can be integral with the reservoir conduit 6 and/or the discharge conduit 10. The exit conduit 12 can be in fluid communication with the reservoir conduit 6 and/or the discharge conduit 10.

Any or all elements of the implantable dialysis device 2 can be made from, for example, a single or multiple stainless steel alloys, nickel titanium alloys (e.g., Nitinol), cobalt-chrome alloys (e.g., ELGILOY® from Elgin Specialty Metals, Elgin, Ill.; CONICHROME® from Carpenter Metals Corp., Wyomissing, Pa.), molybdenum alloys (e.g., molybdenum TZM alloy, for example as disclosed in International Pub. No. WO 03/082363 A2, published 9 Oct. 2003), tungsten-rhenium alloys, for example, as disclosed in International Pub. No. WO 03/082363, polymers such as polyester (e.g., DACRON® from E. I. Du Pont de Nemours and Company, Wilmington, Del.), polypropylene, PTFE, ePTFE, PEEK, Nylon, polyether-block co-polyamide polymers (e.g., PEBAX® from ATOFINA, Paris, France), polyurethanes such as aliphatic polyether polyurethanes (e.g., TECOFLEX® from Thermedics Polymer Products, Wilmington, Mass.), PVC, PAN, PS, polyethersulfone, polyethylene, polymethylmethacrylate (PMMA), thermoplastic, FEP, cellulose (e.g., VISKING®, SERVAPOR®, MEMBRA-CEL®, or SPECTRA/POR® 1, 3 and 6 Dialysis Tubing from SERVA Electrophoresis GmbH of Heidelberg, Germany; Cuprophane PT-150 from Enka-Glanstoff of Germany), such as a seamless regenerated cellulose and CA, extruded collagen, silicone, echogenic, radioactive, radiopaque materials or combinations thereof. Examples of radiopaque materials are barium, sulfate, titanium, stainless steel, nickel-titanium alloys, tantalum and gold.

Any or all elements of the implantable dialysis device 2 can be a matrix for cell ingrowth or used with a fabric, for example a covering (not shown) that acts as a matrix for cell ingrowth. The matrix and/or fabric can be, for example, polyester (e.g., DACRON® from E. I. du Pont de Nemours and Company, Wilmington, Del.), polypropylene, PTFE, ePTFE, nylon, extruded collagen, silicone or combinations thereof.

The elements of the implantable dialysis device 2 and/or the fabric can be filled and/or coated with an agent delivery matrix known to one having ordinary skill in the art and/or a therapeutic and/or diagnostic agent. The agents within these matrices can include radioactive materials; radiopaque materials; cytogenic agents; cytotoxic agents; cytostatic agents; thrombogenic agents, for example polyurethane, cellulose acetate polymer mixed with bismuth trioxide, and ethylene vinyl alcohol; lubricious, hydrophilic materials; phosphor cholene; anti-inflammatory agents, for example non-steroidal anti-inflammatories (NSAIDs) such as cyclooxygenase-1 (COX-1) inhibitors (e.g., acetylsalicylic acid, for example ASPIRIN® from Bayer AG, Leverkusen, Germany; ibuprofen, for example ADVIL® from Wyeth, Collegeville, Pa.; indomethacin; mefenamic acid), COX-2 inhibitors (e.g., VIOXX® from Merck & Co., Inc., Whitehouse Station, N.J.; CELEBREX® from Pharmacia Corp., Peapack, N.J.; COX-1 inhibitors); immunosuppressive agents, for example Sirolimus (RAPAMUNE®, from Wyeth, Collegeville, Pa.), or matrix metalloproteinase (MMP) inhibitors (e.g., tetracycline and tetracycline derivatives) that act early within the pathways of an inflammatory response. Examples of other agents are provided in Walton et al, Inhibition of Prostoglandin $E_2$ Synthesis in Abdominal Aortic Aneurysms, *Circulation*, Jul. 6, 1999, 48-54; Tambiah et al, Provocation of Experimental Aortic Inflammation Mediators and Chlamydia Pneumoniae, *Bit. J. Surgery* 88 (7), 935-940; Franklin et al, Uptake of Tetracycline by Aortic Aneurysm Wall and Its Effect on Inflammation and Proteolysis, *Brit. J. Surgery* 86 (6), 771-775; Xu et al, Sp1 Increases Expression of Cyclooxygenase-2 in Hypoxic Vascular Endothelium, *J. Biological Chemistry* 275 (32) 24583-24589; and Pyo et al, Targeted Gene Disruption of Matrix Metalloproteinase-9 (Gelatinase B) Suppresses Development of Experimental Abdominal Aortic Aneurysms, *J. Clinical Investigation* 105 (11), 1641-1649 which are all incorporated by reference in their entireties. The reservoir 8 can be made from any of the materials disclosed herein for all elements of the implantable dialysis device 2. The reservoir 8 can be made from a biocompatible impermeable membrane. The reservoir 8 can be made from, for example, silicone, cellulose e.g., VISKING®, SERVAPOR®, MEMBRA-CEL®, or SPECTRA/POR®, 1, 3 and 6 Dialysis Tubing from SERVA Electrophoresis GmbH of Heidelberg, Germany; Cuprophane PT-150 from Enka-Glanstoff of Germany), such as a seamless regenerated cellulose and CA, extruded collagen, silicone, polymers, such as PAN, PS, polyethersulfone, polyether ether ketone (PEEK), Nylon, polyether-block co-polyamide polymers (e.g., PEBAX® from ATOFINA, Paris, France), polyurethanes such as aliphatic polyether polyurethanes, (e.g., TECOFLEX® from Thermedics Polymer Products, Wilmington, Mass.), polyvinyl chloride (PVC), poluethylene, polyester (e.g., DACRON® from E. I. Du Pont de Nemours and Company, Wilmington, Del.), polypropylene, PMMA, thermoplastic, fluorinated ethylene propylene (FEP), PTFE, and ePTFE, a metal, such as single or multiple stainless steel alloys, nickel titanium alloys (e.g., Nitinol), cobalt-chrome alloys (e.g., ELGILOY®; CONICHROME®), molybdenum alloys (e.g., molybdenum TZM alloy), tungsten-rhenium alloys, or combinations of any of the above.

The reservoir 8 can be made from an non-permeable material. The reservoir 8 can be made from a material having a thickness and construction such that the material can remain intact without leaking or becoming substantially permeable during conditions of extreme acceleration, for example in a halting car accident at about 89 km/h (55 miles per hour) producing, for example, an acceleration of about 991.5 m/s$^2$ (3,253 f/s$^2$). The reservoir 8 can be made from a multi-layer and/or fiber-reinforced material. The reservoir 8 can be made from a rigid material. The reservoir 8 can be made from any material listed herein, for example, polymers such as polyester (e.g. DACRON® from E. I. Du Pont de Nemours and Company, Wilmington, Del.), polypropylene, polytetrafluoroethylene (PTFE) (e.g., TEFLON®, E. I. Du Pont de Nemours and Company, Wilmington, Del.), expanded PTFE (ePTFE) (e.g., GORE-TEX® from W.L. Gore & Associates, Inc., Newark, Del.), polyether ether ketone (PEEK), Nylon, polyether-block co-polyamide polymers (e.g., PEBAX® from ATOFINA, Paris, France), polyurethanes such as aliphatic polyether-polyurethanes (e.g., TECOFLEX® from Thermedics Polymer Products, Wilmington, Mass.), PVC, PAN, PS, polyethersulfone, polyethylene, PMMA, thermoplastic, FEP, cellulose (e.g., VISKING®, SERVAPOR®, MEMBRA-CEL®, or SPECTRA/

POR® 1, 3 and 6 Dialysis Tubing from SERVA Electrophoresis GmbH of Heidelberg, Germany; Cuprophane PT-150 from Enka-Glanstoff of Germany), such as a seamless regenerated cellulose and/or CA, extruded collagen, silicone or combinations thereof.

The implantable dialysis device 2 can have one or more reservoir sensors 22. The reservoir sensors 22 can be in the reservoir 8, and/or in the reservoir connector 18, and/or in the reservoir conduit 6. The reservoir sensors 22 can be configured to measure pressure, pH, temperature, electrolyte concentration, analyte concentration, or combinations thereof in the reservoir 8.

The implantable dialysis device 2 can have one or more peritoneal cavity sensors 36. The peritoneal cavity sensors 36 can be on the discharge conduit 10, for examples, at the discharge conduit first end 32a and/or along the discharge conduit length 34. The peritoneal cavity sensors 36 can be configured to measure pressure, pH, temperature, electrolyte concentration, analyte concentration, or combinations thereof in the peritoneal cavity.

The implantable dialysis device 2 can have one or more bladder sensors 48. The bladder sensors 48 can be on the exit 14. The bladder sensors 48 can be configured to measure pressure, pH, temperature, electrolyte concentration, analyte concentration, or combinations thereof in the bladder. The sensors 22, 36, and 48 can measure concentration of dialysate solutes in the fluids. The sensors 22, 36, and 48 can send signals indicating respective measured metrics to the distributor 4.

Figure 2:
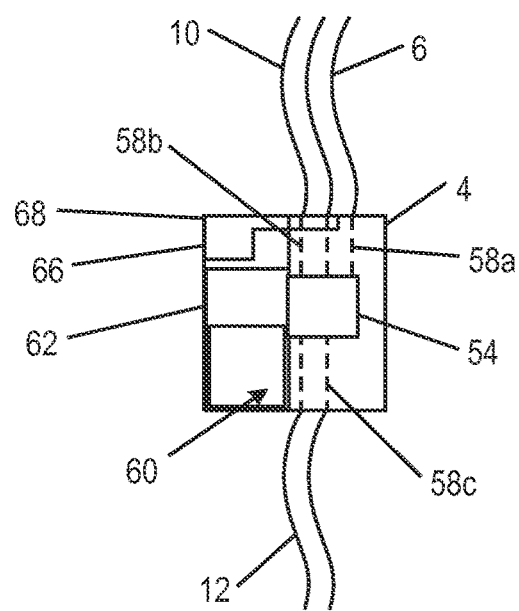
FIG. 2 illustrates cross-section A-A of an embodiment of the distributor.

FIG. 2 illustrates that the distributor 4 can have a pump 54. The pump 54 can be a mechanical, electromechanical, osmotic or diffusion pump, or combinations thereof. The pump 54 can be a hand-powered pump, for example the pump can be a resilient, compressible bulb pump. The pump 54 can be a miniature gear-pump. The pump 54 can be strong enough to clear clogs from the discharge conduit 10 and/or the exit conduit 12. The pump 54 can produce a flow rate in the discharge conduit 10 from about 50 mL/min. (3.0 in.$^3$/min.) to about 5000 mL/min. (300 in.$^3$/min.), more narrowly from about 250 mL/min. (15 in.$^3$/min.) to about 500 mL/min. (30 in.$^3$/min.). The flow rate can be set to prevent bladder spasm with the rapid influx of the fluid.

The pump 54 can have and/or be in fluid communication with a distributor valve 56 (shown infra). The distributor valve 56 can be a mechanical valve, a semi-permeable membrane or combinations thereof. The distributor valve 56 can be a single, three-way valve.

The distributor 4 can have a distributor first conduit 58a. The distributor first conduit 58a can be in fluid communication with the reservoir conduit second end 20b. The distributor first conduit 58a can be in fluid communication with the distributor valve 56. The distributor first conduit 58a can be integral with the reservoir conduit second end 20b.

The distributor 4 can have a distributor second conduit 58b. The distributor second conduit 58b can be in fluid communication with the discharge conduit 10. The distributor second conduit 58b can be in fluid communication with the distributor valve 56. The distributor second conduit 58b can be integral with the discharge conduit 10.

The distributor 4 can have a distributor third conduit 58c. The distributor third conduit 58c can be in fluid communication with the exit conduit first end 42a. The distributor third conduit 58c can be in fluid communication with the distributor valve 56. The distributor third conduit 58c can be integral with the exit conduit first end 42a.

The distributor valve 56 can be configured to route flow between a distributor first conduit 58a, the distributor second conduit 58b, and the distributor third conduit 58c. The distributor valve 56 can be configured as a one-way flow or check valve, for example, preventing backflow in any direction. The distributor valve 56 can be a one-way valve preventing flow in the direction from the distributor third conduit 58c to either the distributor first conduit 58a or the distributor second conduit 58b.

The distributor valve 56 can be a pressure sensing valve. The distributor valve 56 can be configured to shut off flow if backpressure exceeds a pre-determined threshold. If pressure in the peritoneal cavity is less than about 1.5 kPa (0.15 psi), more narrowly less than about 1 kPa (0.1 psi), yet more narrowly less than about 0.5 kPa (0.07 psi), then the pump 54 can be inhibited (e.g., stopped or slowed), for example be the distributor valve 56 and/or a controller. If the absolute pressure in the bladder is greater than or equal to about 3 kPa (0.4 psi), more narrowly, greater than or equal to about 4 kPa (0.6 psi), then the pump 54 can be inhibited. If the differential between the pressure is the peritoneal cavity and the pressure to the bladder pressure is greater than or equal to about 2 kPa (0.3 psi), more narrowly greater than or equal to about 3 kPa (0.4 psi), then the pump 54 can be inhibited.

The distributor 4 can have a power storage and/or regulation device, for example a battery 60. The battery 60 can be configured to supply power to the pump 54 and/or the distributor valve 56. The battery 60 can be one or more power storage devices (not shown), for example capacitors, dry or wet cells, flywheels, springs, or combinations thereof. The battery 60 can hold a charge of more than about 500 mAh, for example about 1000 mAh. For example 3 AA Nickel Cadmium about 1000 mAh batteries can be used. The battery 60 can be configured to provide a current of greater than about 0.2 DCA and/or less than about 2.0 DCA, for example about 0.42 DCA.

The distributor 4 can have an internal transducer 62. The internal transducer 62 can receive energy in a first form (e.g. moving magnetic fields), convert the energy into a second form (e.g., direct current electricity), and deliver the second form of energy to appropriate elements (e.g., pump 54, distributor valve 56, controller) in the implantable dialysis device 2. The internal transducer 62 can be wholly or partially inside a distributor case. An internal transducer connector 64 (shown infra) can be configured to deliver the energy to the appropriate elements. The internal transducer connector 64 can be wholly within the distributor case.

The distributor 4 can have an internal filing port 66. The internal filling port 66 can have a self-sealing membrane forming at least part of the external wall of the distributor 4. The internal filling port 66 can be configured to receive injections (e.g., of dialysate solution and/or other agent), for example from a transcutaneous needle. The internal filling port 66 can have a locating mechanism, for example, a magnetic field or another signal generating mechanism. The locating mechanism can aid targeting the internal filling port 66, for example, when injecting dialysate solution and/or other agent. The internal filling port 66 can have a storage volume. The internal filling port 66 can have a non-corrosive internal surface. The internal filling port 66 can be a receptacle for a cartridge or ampoule. A filling conduit 68 can be configured to create fluid communication between the internal filling port 66 and the reservoir conduit 6.

Figure 3:
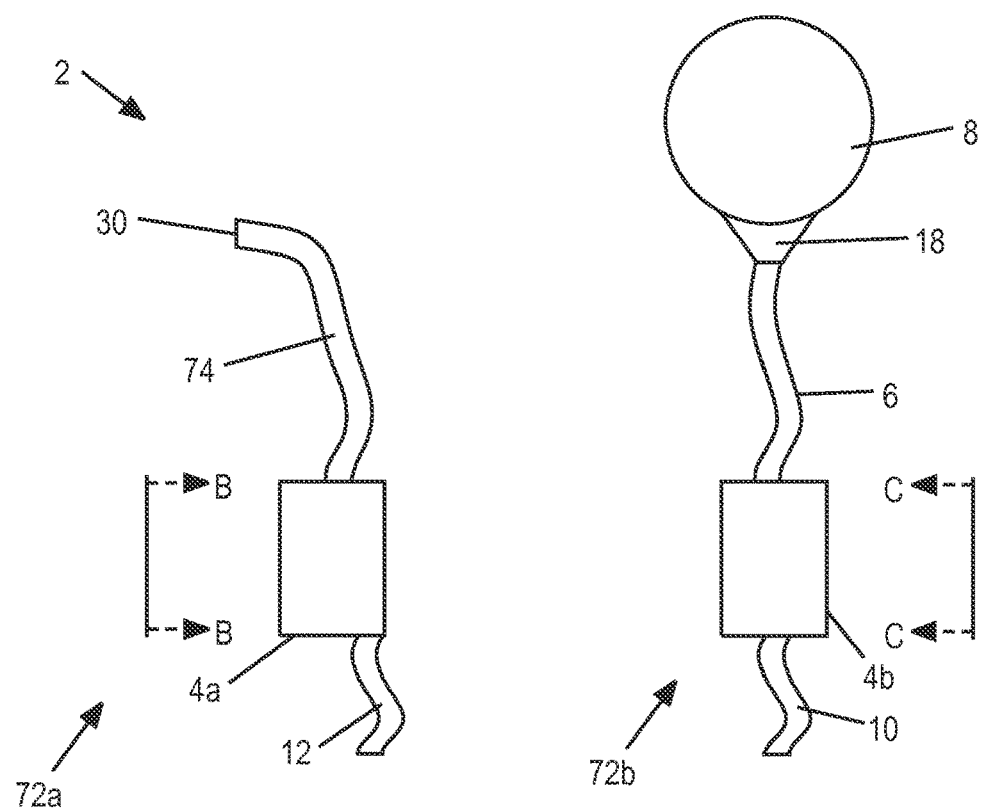
FIG. 3 illustrates an embodiment of the implantable dialysis device.

FIG. 3 illustrates the implantable dialysis device 2 that can have a first component 72a and a second component 72b. The first component 72a can be physically unattached to the second component 72b.

The first component 72a can be configured to pump fluid from a drainage conduit 74 to, and out, the exit conduit 12. The drainage conduit 74 can have a drainage conduit first port 75. The first component 72a can have a first distributor 4a. The first distributor 4a can be attached to the drainage conduit 74. The first distributor 4a can be attached to the exit conduit 12.

The second component 72b can be configured to receive a solution, for example, dialysate by injection into a second distributor 4b. The second component 72b can be configured to deliver and store the solution in the reservoir 8. The second component 72b can be configured to deliver the stored solution from the reservoir 8 to, and out, the discharge conduit 10.

The second distributor 4b can be attached to the reservoir conduit 6 and the reservoir 8. The second distributor 4b can be attached to the discharge conduit 10.

The first component 72a can be in data and/or power communication with the second component 72b. One or more wires (not shown) can attach the first component 72a to the second component 72b. The first component 72a can communicate with the second component 72b over a data network, for example, a wired and/or wireless network, such as Ethernet (IEEE 802.3), Firewire (IEEE 1394), 802.11 (wireless LAN), Bluetooth, cellular communication, serial port (RS-232, RS-485), parallel port (IEEE 1284), Fiber Channel, IRDA infrared data port, radio such as 900 MHz RF or FM signal, or combinations thereof.

Any implantable dialysis device 2 can also use the communication networks supra to communicate data with an extracorporeal component, for example, a monitoring device such as a handheld diagnostic computer or peripheral device (e.g., a personal data assistant). The extracorporeal component can transmit and receive data and/or energy from the implantable dialysis device 2 (e.g., from the internal transducer 62 and/or controller and/or battery 60). The extra corporeal component can be used to control operation of, or provide an energy charge to, the implantable dialysis device 2.

Figure 4:
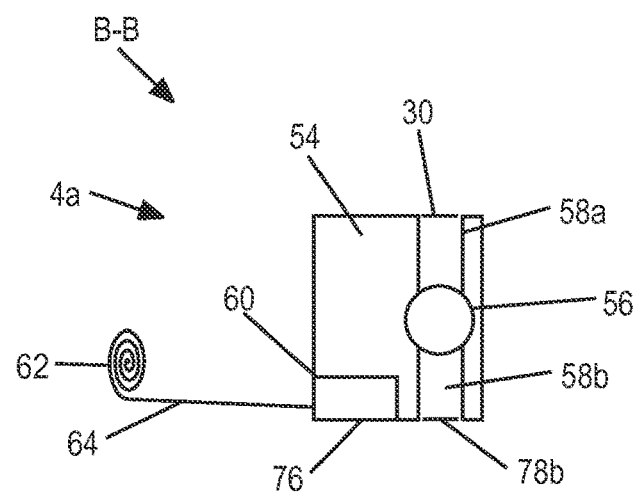
FIG. 4 illustrates cross-section B-B of an embodiment of the distributor.

FIG. 4 illustrates the first distributor 4a that can have no internal filling port 66. The first distributor 4a can have no distributor third conduit 58c. The exterior of the distributor 4 can be the distributor case 76. The distributor case 76 can be made from, coated, or otherwise surrounded with a biocompatible material.

The distributor 4 can have a distributor first port 78a and a distributor second port 78b. The distributor ports 78a and 78b can be voids in the distributor case 76, semi-permeable membranes, permeable membranes, or combinations thereof. The distributor first port 78a can be fixedly or releasable attached to a conduit, for example, the drainage conduit 74. The distributor second port 78b can be fixedly or releasably attached to a conduit, for example the exit conduit 12.

A distributor first port 78a can be fixedly or releasably attached to and/or integral with, and in fluid communication with, the drainage conduit 74. A distributor second port 78b can be fixedly or releasably attached to and/or integral with, and in fluid communication with, the exit conduit 12. The distributer valve 56 can be a one-way check valve permitting flow from the distributor first port 78a to the distributor second port 78b, but preventing or minimizing flow from the distributor second port 78b to the distributor first port 78a.

The internal transducer 62 can be outside the distributor case 76. The internal transducer 62 can be an induction coil. The internal transducer connector 64 can connect the internal transducer 62 to the pump 54 and/or to one or more power storage devices (not shown), for example capacitors, dry or wet cells, flywheels, springs, or combinations thereof. The internal transducer connector 64 can pass through the distributor case 76.

For implantable dialysis devices 2 that have more than one distributor 4, any or each distributor 4 can have a separate pump 54.

Figure 5:
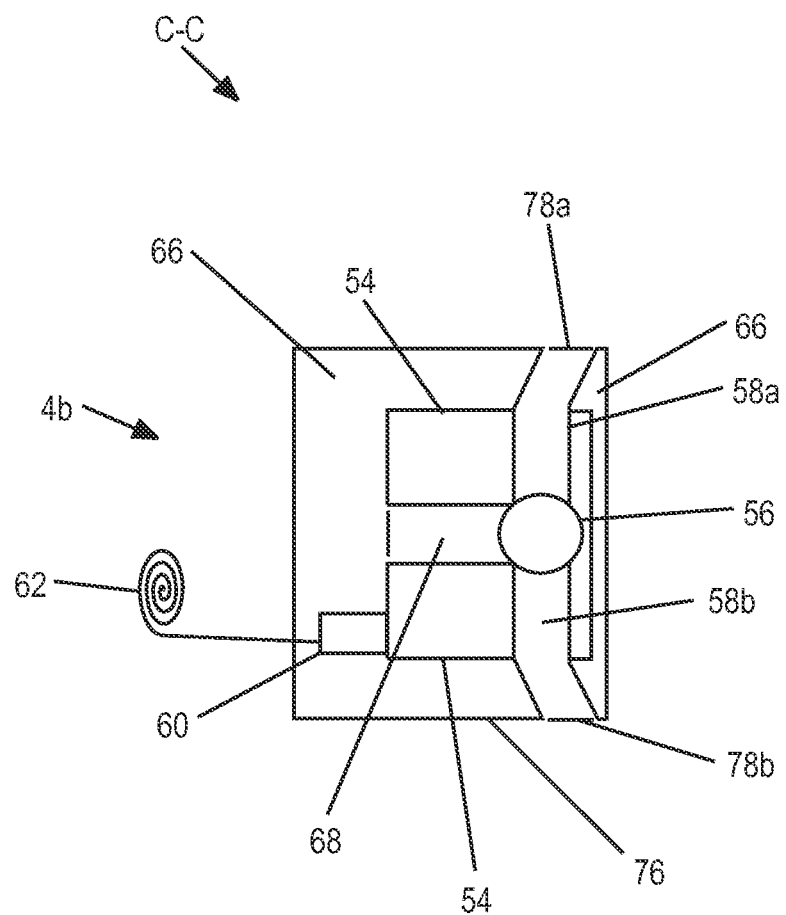
FIG. 5 illustrates cross-section C-C of an embodiment of the distributor.

FIG. 5 illustrates that the second distributor 4b can have the storage volume of the internal filling port 66 surrounding the pump 54. The distributor case 76 can be a self-sealing material configured to allow a needle puncture in one or more locations.

The reservoir conduit second end 20b (not shown) can be fixedly or releasably attached to and/or integral with, and in fluid communication with, the distributor first port 78a. The discharge conduit second end 32b (not shown) can be fixedly or releasably attached to and/or integral with, and in fluid communication with, the distributor second port 78b.

Figure 6:
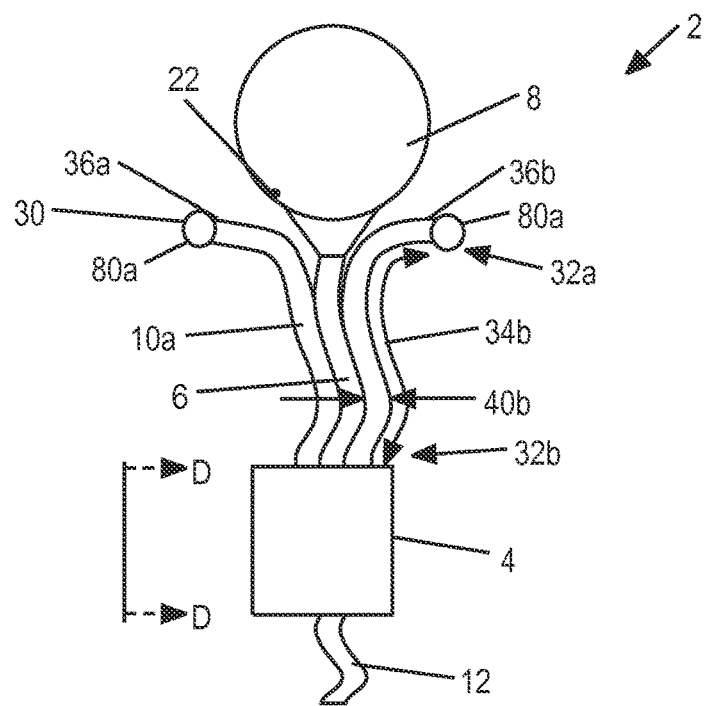
FIG. 6 illustrates an embodiment of the implantable dialysis device.

FIG. 6 illustrates the implantable dialysis device 2 that can have a first discharge conduit 10a and a second discharge conduit 10b. The first and second discharge conduits 10a and 10b can have first and second discharge conduit lengths 34a and 34b and first and second discharge conduit diameters 40a and 40b that can be equivalent to those supra for the discharge conduit 10. The first and/or second discharge conduits 10a and/or 10b can have first and/or second peritoneal cavity sensors 36a and/or 36b, respectively.

The first and/or second discharge conduits 10a and/or 10b can have a first and/or second discharge conduit first port guards 80a and/or 80b. The guards 80a and 80b can be rigid, semi-rigid or flexible. The port guards 80a and 80b can be wire screens, permeable membranes, or combinations thereof. The port guards 80a and 80b can be configured to filter particles based on size and/or charge.

Figure 7:
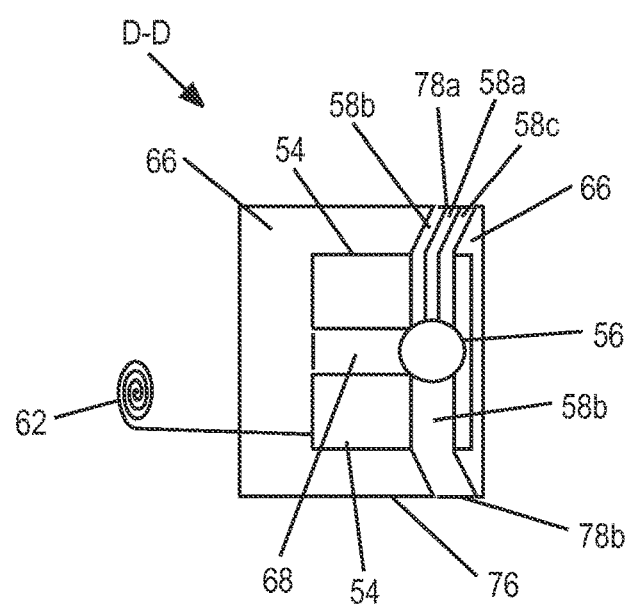
FIG. 7 illustrates cross-section D-D of an embodiment of the distributor.

FIG. 7 illustrates that the distributor 4 can have the distributor first conduit 58a, the distributor second conduit 58b, and the distributor third conduit 58c that can be segmented from a single channel, and/or be adjacent to each other. The distributor first, second, and third conduits 58a, 58b and 58c can all open on the same side of the distributor 4. The distributor 4 can have a distributor fourth conduit 58d. The distributor fourth conduit 58d can open a different side of the distributor 4 than the first, second and third conduits 70a, 70b and 70c.

The reservoir conduit second end 20b can be fixedly or releasable attached to and/or integral with, and in fluid communication with, the distributor first conduit 58a. The first discharge conduit second end 32b' can be fixedly or releasably attached to and/or integral with, and in fluid commutation with, the distributor second conduit 58b. The second discharge conduit second end 32b can be fixedly or releasably attached to and/or integral with, and in fluid communication with, the distributor third conduit 58c. The fourth conduit 58d can be fixedly or releasably attached to and/or integrated with, and in fluid communication with, the exit conduit 12.

Figure 8:
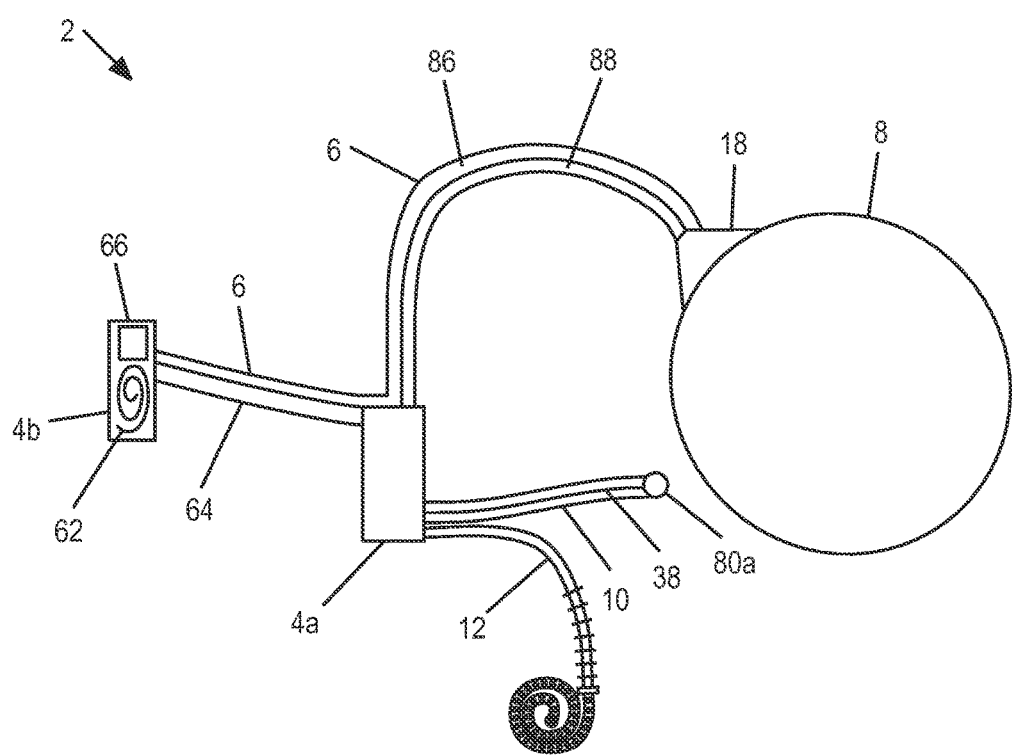
FIG. 8 illustrates an embodiment of the implantable dialysis device.

FIG. 8 illustrates that the implantable dialysis device 2 can have the first and second distributors 4a and 4b. The reservoir conduit 6 can have an inflow channel 86 and an outflow channel 88.

The inflow and outflow channels 86 and 88 can be separated by a septum, be otherwise attached or integral, or be contained within two distinct, and separate tubes. The inflow channel 86 can be attached to the outflow channel 88 along pert or all of the lengths of the inflow channel 86 and the outflow channel 88.

The inflow channel 86 can provide fluid communication between the internal filling port 66 and the reservoir 8. The internal filling port 66 and/or filling conduit (not shown in FIG. 8) can be attached to the inflow channel 86. The reservoir 8 and/or the reservoir connector 18 can be attached to the inflow channel 86. The inflow channel 86 can be attached to and/or integral with the reservoir 8 and the second distributor 4*b*, for example with the internal filling port 66. The inflow channel 86 can be in direct fluid communication with, and/or attached to, the first distributor 4*a*. The first distributor 4*a* can be configured to provide a positive and/or negative pressure to the inflow channel 86.

The outflow channel 88 can be is direct fluid communication with, and attached to and/or integral with the first distributor 4*a* and the reservoir 8 and/or the reservoir connector 18.

The discharge conduit 10 can have one or more perforations 38 along part or all of the discharge conduit length 34. The perforations 38 can be along the discharge conduit first end 32*a* and/or along the discharge conduit second end 32*b*. The perforations 38 can be configured to allow the fluid communication of dialysate solute. The perforations 38 can be configured to disallow fluid communication of proteins. The perforations 38 can be configured to disallow fluid communication of dialysate solute.

The first distributor 4*a* can have the pump 54 (not shown). The second distributor 4*b* can have the internal filling port 66. The second distributor 4*b* can have the internal transducer 62. The internal transducer connector 64 can be attached to the first distributor 4*a* and/or the second distributor 4*b*. The internal transducer connector 64 can transfer power from the second distributor 4*b* to the first distributor 4*a*. The first and/or second distributors 4*a* and/or 4*b* can have the batteries 60 (not shown in FIG. 8).

Figure 9:
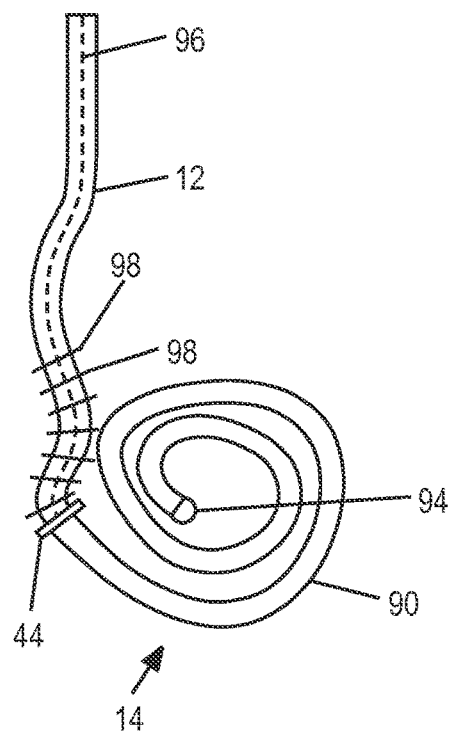
FIG. 9 illustrates an embodiment of the exit conduit and the exit.

FIGS. 8 and 9 illustrate that the exit conduit 12 can have an exit extension 90. The exit extension 90 can be semi-permeable, permeable, impermeable, or combinations thereof. The exit extension 90 can have a length of conduit, for example a coiled or "pigtail" catheter. The exit extension 90 can have one or more exit ports 46. The exit extension 90 can have an exit tip 94. The exit tip 94 can have the exit port 46 (not shown in FIG. 8 or 9). The exit tip 94 can be semi-permeable, impermeable, permeable, or combinations thereof.

The exit conduit 12 can have an exit conduit longitudinal axis 96. The exit conduit 12 can have one or more sub-anchors 98. The sub-anchors 98 can be substantially perpendicular to the exit conduit longitudinal axis 96. The anchor 44 can be substantially perpendicular to the exit conduit longitudinal axis 96. The sub-anchors 98 can be flanges. The sub-anchors 98 can be rigid or flexible.

Figure 10:
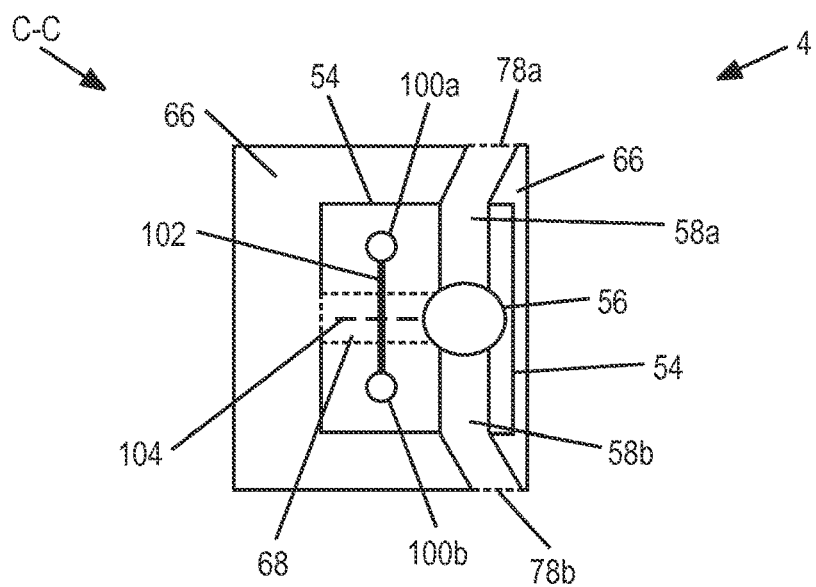
FIG. 10 illustrates cross-section C-C of an embodiment of the distributor.

FIG. 10 illustrates that the pump 54 can have or be mechanically attached to a rotational electromechanical motor 99. The motor 99 can be configured to be inductively driven. The motor 99 can have a first pole 100*a* and a second pole 100*b*. A pole axle 102 can attach the first pole 100*a* to the second pole 100*b*. The pole axle 102 can rotate about a motor rotation axis 104, for example when the first and second poles 100*a* and 100*b* are urged by a dynamic external magnetic field. The pole axle 102 can be mechanically coupled to a flow driving mechanism (not shown). The pump 54 and/or motor 99 can be the taught by PCT Patent Application titled Magnetic Circumferentially Coupled Implantable Pump, filed 18 Aug. 2004, and hereby incorporated by reference in its entirety.

Figure 11:
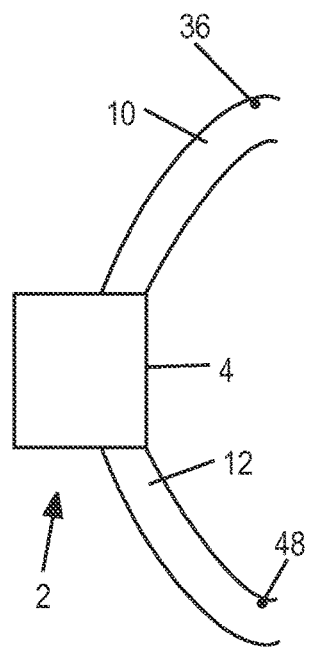
FIGS. 11-13 illustrate various embodiments of the implantable dialysis device.
Figure 12:
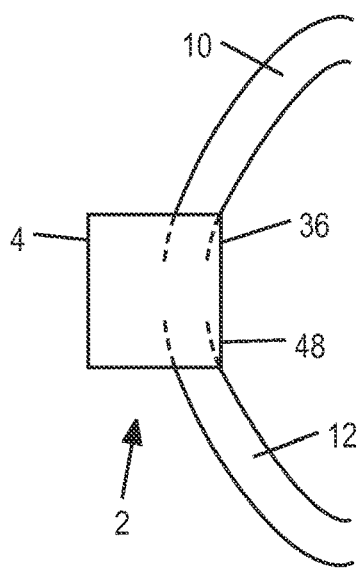
Figure 13:
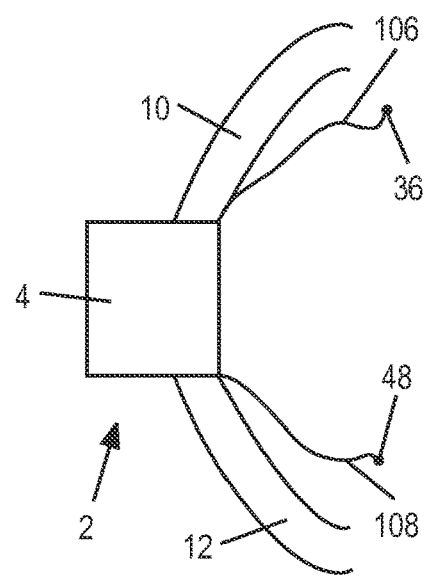

FIGS. 11 through 13 (not showing elements of the implantable dialysis device 2 for clarity) illustrate various configurations of the peritoneal cavity sensor 36 and bladder sensor 48. The peritoneal cavity sensor 36 and bladder sensor 48 can be in fluid communication with the discharge conduit 10 and/or exit conduit 12, respectively (i.e., and the peritoneal cavity and the bladder, respectively, during use). As shown in FIG. 11, the peritoneal cavity sensor 36 and bladder sensor 48 can be attached to the discharge conduit 10 and exit conduit 12. The peritoneal cavity sensor 36 and the bladder sensor 48 can be on the inside (as shown) and/or outside of the discharge and exit conduits 10 and 12. As shown in FIG. 12, the peritoneal cavity sensor 36 and bladder sensor 48 can be located in the distributor 4. As shown in FIG. 13, the peritoneal cavity sensor 36 can be attached to a peritoneal tether 106. The bladder sensor 48 can be attached to a bladder tether 108. Multiple sensors 36 and 48 can be attached to each tether 106 and 108. The tethers 106 and 108 can be attached to the respective conduits 10 and 12, and/or the distributor 4, and/or to other elements of the implantable dialysis device 2. The tethers 106 and 108 can be flexible or rigid.

The implantable dialysis device 2 can have more than one of each peritoneal cavity sensor 36 and bladder sensor 48. The peritoneal cavity sensor 36 and bladder sensor 48 can be in any combination of configurations.

Figure 14:
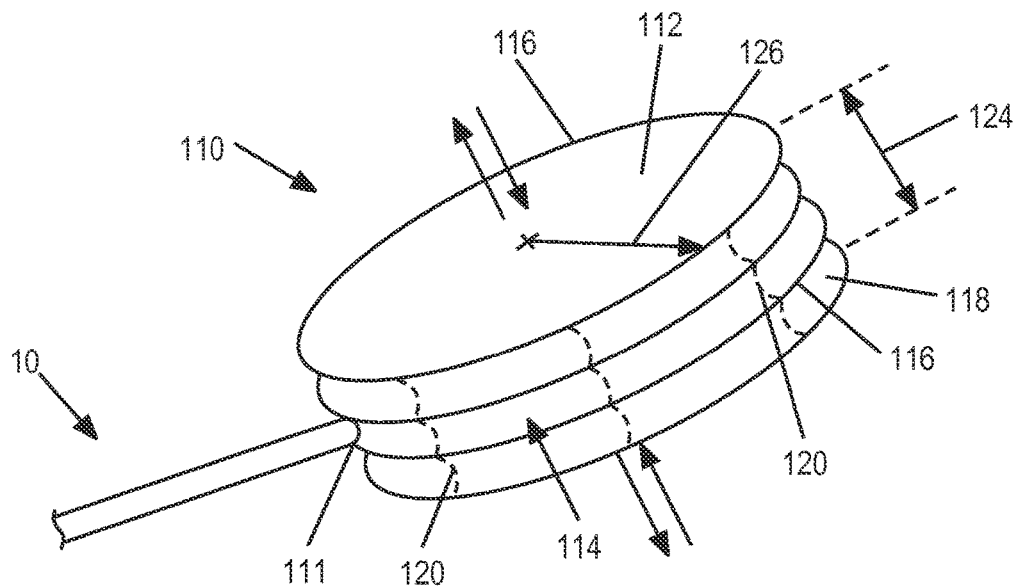
FIGS. 14 and 15 illustrate various embodiments of the transfer element.
Figure 15:
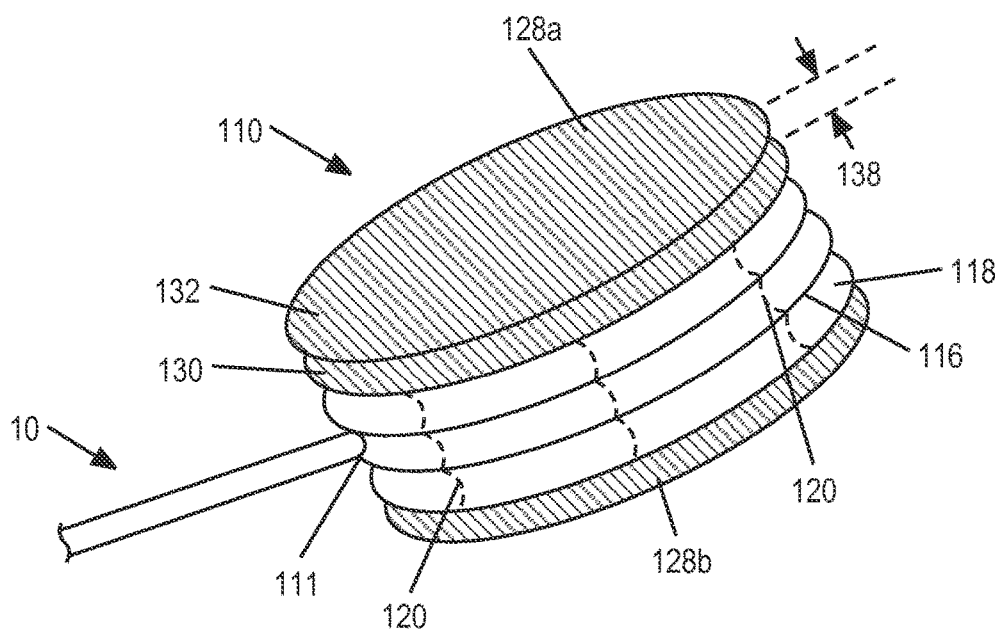

FIGS. 14 and 15 illustrate that the implantable dialysis device 2 can have a transfer element 110 at the first end of the drainage (e.g., shown without the transfer element 110 in FIG. 3) and/or discharge (e.g., shown without the transfer element 110 in FIG. 6) conduits 74 and/or 10. The transfer element 110 can be integral with, and/or attached to, the conduits 74 and/or 10 via a transfer element connector 111. The transfer element 110 can have a permeable surface. The transfer element 110 can be configured to filter peritoneal fluids across a transfer element face 112. The transfer element 110 can be configured to filter fluid across the transfer element face 112 through size and/or charge exclusion. The transfer element 110 can be configured to allow water and waste in the peritoneal fluid to osmotically transfer into the transfer element 110.

FIG. 14 illustrates that the transfer element 110 can be configured to resiliently expand and compress, as shown by arrows. The transfer element 110 can be configured to transfer liquids out of the transfer element 110 and into the drainage and/or discharge conduits 74 and/or 10. The transfer element 110 can be biased to stay in an expanded configuration at rest. The transfer element 110 can be hollow. The hollow inside the transfer element 110 can be in fluid communication with the drainage and/or discharge conduits 74 and/or 10. A one-way valve (not shown) in the drainage and/or discharge conduits 74 and/or 10, the transfer element connector 111, or the transfer element 110, can be configured to prevent or minimize fluid communication from the drainage and/or discharge conduits 74 and/or 10 to the reservoir 8. The transfer element 110 can have a substantially cylindrical configuration.

The transfer element 110 can have a transfer element face 112. The transfer element 110 can have two or more transfer element faces 112. The transfer element faces 112 can be made from a substantially impermeable, semi-permeable, permeable material, or combinations thereof. The transfer element face 112 can be configured to be substantially or wholly permeable to dialysate solutes. The transfer element face 112 can be substantially or wholly impermeable to proteins. The transfer element face 112 can be made from the materials listed herein, for example, polyester (e.g., DACRON® from E. I. Du Pont de Nemours and Company, Wilmington, Del.), polypropylene, PTFE (e.g., TEFLON®, E. I. Du Pont de Nemours and Company, Wilmington, Del.), ePTFE (e.g., GORE-TEX® from W.L. Gore & Associates, Inc., Newark, Del.), PEEK, Nylon, polyether-block co-polyamide polymers (e.g., PEBAX® from ATOFINA, Paris, France), polyurethanes such as aliphatic polyether polyurethanes (e.g., TECOFLEX® from Thermedics Polymer Products, Wilmington, Mass.), polyvinyl chloride (PVC), PAN, PS, polyethersulfone, polyethylene, PMMA, thermoplastic, FEP, cellulose (e.g., VISKING®, SERVAPOR®, MEMBRA-CEL®, or SPECTRA/POR® 1, 3 and 6 Dialysis Tubing from SERVA Electrophoresis GmbH of Heidelberg, Germany; Cuprophane PT-150 from Enka-Glanstoff of Germany), such as a seamless regenerated cellulose and CA, extruded collagen, silicone, echogenic, radioactive, radiopaque materials or combinations thereof. Any of the polymers can be permeable if woven loosely enough, as known to those having ordinary skill in the art.

The transfer element faces 112 can be made from a porous membrane. The transfer element faces 112 can have pores having diameters substantially smaller than about 500 µm (19.7 mil), yet more narrowly from about 5 µm (0.2 mil) to about 200 µm (7.87 mil). ("Substantially smaller" is having about 95% or more of the pores being smaller.) The transfer element faces 112 can have an average pore diameter from about 5 µm (0.2 mil) to about 500 µm (1.97 mil), for example about 10 µm (0.39 mil). The transfer element faces 112 can contain pores having diameters less than about 10 mm (0.4 in.), more narrowly less than about 5 mm (0.2 in.). For example the pores can have diameters less than about 2 mm (0.08 in.), more narrowly less than about 1 mm (0.04 in.), yet still more narrowly less than about 0.5 mm (0.02 in.). For example the pores can have diameters of about 2 mm (0.08 in.).

The transfer element 110 can have a transfer element side 114. The transfer element side 114 can be made from a substantially impermeable, semi-permeable, permeable material, or combinations thereof. The transfer element side 114 can be configured to be substantially or wholly permeable to dialysate solutes. The transfer element side 114 can be substantially or wholly impermeable to proteins. The transfer element sides 114 can be made from a material that has a permeability that is not substantially effected by expansion and contraction. The transfer element side 114 can be made from materials listed herein, for example the materials listed for the transfer element faces 112.

The transfer element side 114 can be made from one or more material listed infra for making the transfer element faces 112.

The transfer element 114 can have one or more transfer element frames 116. The frames 116 can be wires or filaments. The frames 116 can be rigid, flexible, resilient, deformable, or combinations thereof. The frames 116 can be made from, for example, Nitinol or stainless steel. The frames 116 can be circular, oval, triangular, square, pentagonal, hexagonal, or combinations thereof. The frames 116 can be on the outside of, the inside of, embedded into, or any combinations thereof with, the material on the surface of the transfer element 110.

The transfer element side 114 can have one or more bellows 118. The transfer element side 114 can have about three bellows 118. The bellows 118 can be covered by a flexible material. Each bellow 118 can have one frame 116 on each side of the bellow 118.

The transfer element 110 can have one or more struts 120. The struts 120 can provide resiliency to the transfer element 110. When the transfer element 110 is in the expanded configuration, the struts 120 can be fully extended and/or straight or slightly curved. The struts 120 can attach a first frame 116a to a second frame 116b. One strut 120 can attach to all of the frames 116. One strut 120 can attach to the frame 116 on a first transfer element face 112 and the frame 116 on a second transfer element face 112.

The transfer element 110 can be resilient. During use, the resiliency of the transfer element 110 can produce a slow and steady negative pressure in the peritoneal cavity. The negative pressure can be from about −500 mmHG (−10 psi) to about −5 mmHg (−0.1 psi), more narrowly from about −300 mm Hg (−6 psi) to about −50 mmHg (−1 psi), for example −500 mmHg (−10 psi), about −300 mm Hg (−6 psi), about −50 mmHg (−1 psi), or about −5 mmHg (−0.1 psi).

The transfer element 110 can have a transfer element height 124. The transfer element height 124 can be from about 0 cm (0 in.) to about 8 cm (3 in.), more narrowly from about 1 cm (0.4 in.) to about 4 cm (2 in.), for example about 0 cm (0 in.), about 1 cm (0.4 in.), about 2 cm (0.8 in.), about 4 cm (2 in.), or about 8 cm (3 in.).

The transfer element 110 can have a transfer element radius 126. The transfer element radius 126 can vary over the transfer element height 124. The transfer element radius 126 can be from about 1 cm (0.4 in.) to about 10 cm (4 in.), more narrowly from about 2 cm (0.8 in.) to about 4 cm (2 in.), for example about 1 cm (0.4 in.), about 2 cm (0.8 in.), about 4 cm (2 in.), or about 10 cm (4 in.).

FIG. 15 illustrates that the reservoir can have a first barrier 128a and/or a second barrier 128b. The transfer element 110 can have more than two barriers 128. The barriers 128 can have barrier sides 130. The barrier sides 130 can be rigid or flexible. The barriers 128 can have barrier faces 132. The barrier faces 132 can be supported away from the transfer element faces 112, for example, by the barrier sides 130. The barrier faces 132 can be in contact with the transfer element faces 112.

The barriers 128 can be made from a substantially impermeable, semi-permeable, permeable material, or combinations thereof. The barriers 128 can be configured to be substantially or wholly permeable to dialysate solutes. The barriers 128 can be substantially or wholly impermeable to proteins. The barriers 128 can be made from, for example, polymers such as polyester (e.g., DACRON® from E. I. Du Pont de Nemours and Company, Wilmington, Del.), polypropylene, PTFE (e.g., TEFLON®, E. I. Du Pont de Nemours and Company, Wilmington, Del.), ePTFE (e.g., GORE-TEX® from W.L. Gore & Associates, Inc., Newark, Del.), PEEK, Nylon, polyether-block co-polyamide polymers (e.g., PEBAX® from ATOFINA, Paris, France), polyurethanes such as aliphatic polyether polyurethanes (e.g., TECOFLEX® from Thermedics Polymer Products, Wilmington, Mass.), PVC, PAN, PS, polyethersulfone, polyethylene, PMMA, thermoplastic, FEP, cellulose (e.g., VISKING®, SERVAPOR®, MEMBRA-CEL®, or SPECTRA/POR® 1, 3 and 6 Dialysis Tubing from SERVA Electrophoresis GmbH of Heidelberg, Germany; Cuprophane PT-150 from Enka-Glanstoff of Germany), such as a seamless regenerated cellulose and CA, extruded collagen, silicone, echogenic, radioactive, radiopaque materials or combinations thereof.

The barriers 128 and/or the transfer element faces 112 and/or the transfer element side 114 can be electrically charged, for example negatively charged. Conductive filaments (not shown) can be sewn, fused, embedded, or otherwise attached into, onto, or under the barriers 128, and/or the transfer element faces 112, and/or the transfer element sides 114. The materials used to make the barriers 128, and/or the transfer element faces 112, and/or the transfer element sides 114 can be embedded and/or partially or substantially coated with a conductive material. The conductive material and/or conductive filament can be statically charged before deployment, and/or receive a charge from the distributor 4 and/or another energy source during use. The charge on the barriers 128 and/or the transfer element faces 112 and/or the transfer elements side 114 can repel proteins. The barriers 128 can be made from a conductive material, for example a metal. The conductive material can be in electrical current communication, for example directly or inductively, with the power storage device, for example the battery 60. The conductive material can generate a low-level charge on the barriers 128. The low-level charge on the barriers 128 can repel charged particles, for example proteins.

The barriers 128 can have a barrier height 138. The barrier height 138 can be from about 0 mm (0 in.) to about 10 mm (0.4 in.), more narrowly from about 1 mm (0.04 in.) to about 5 mm (0.2 in.), yet more narrowly from about 2 mm (0.08 in.), to about 5 mm (0.2 in.), for example about 0 mm (0 in.), about 1 mm (0.04 in.), about 2 mm (0.08 in.), about 5 mm (0.2 in.) or about 10 mm (0.4 in.).

In some embodiments of the implantable dialysis device 2, the distributor valve 56 can be a one-way valve, and the implantable dialysis device 2 can have no pump 54. The distributor valve 56 can have a semi-permeable membrane between the internal filling port 66 and the distributor first conduit 58a.

Method of Use

Figure 16:
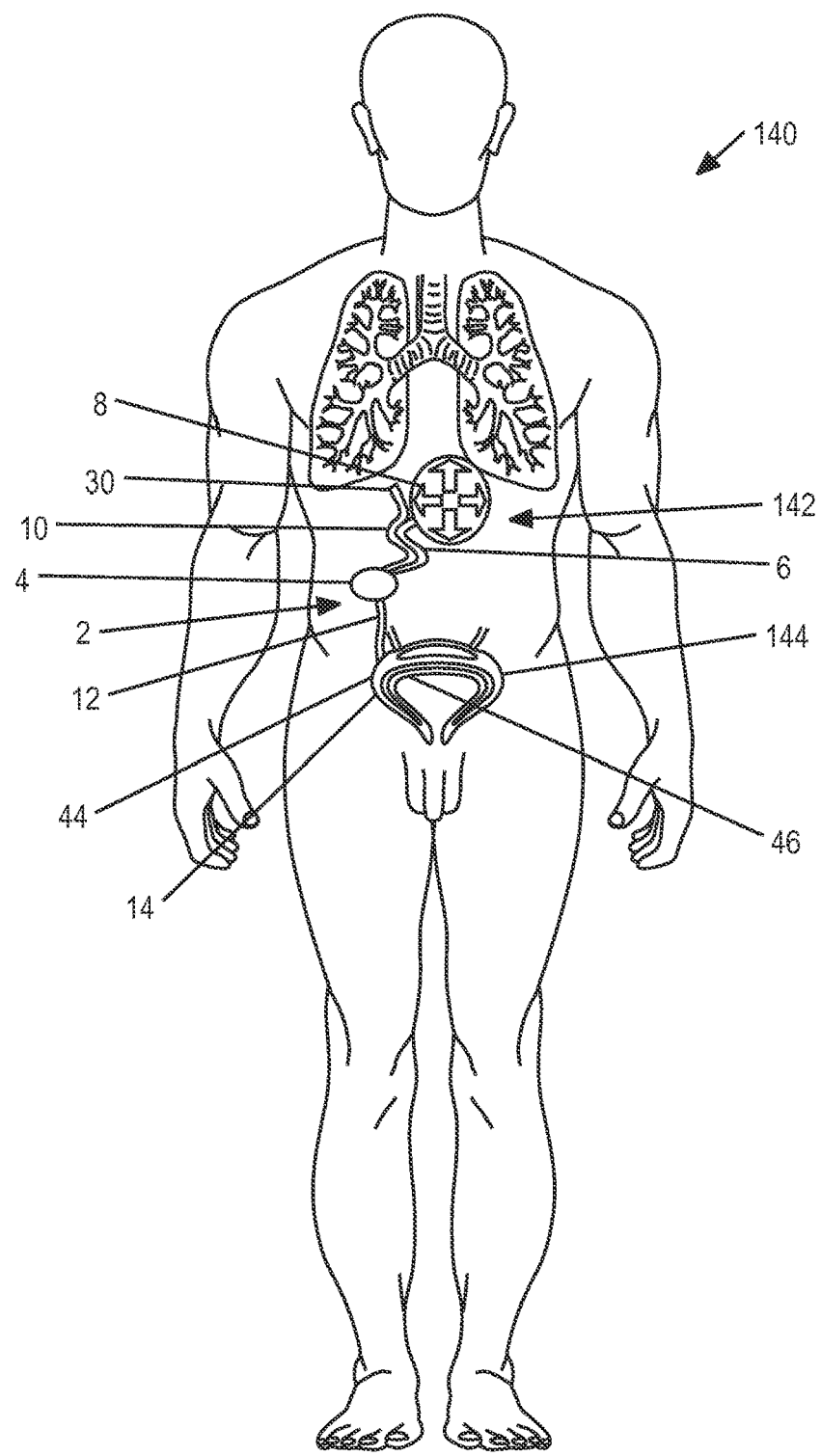
FIG. 16 illustrates a method and placement for implanting the implantable dialysis device.

FIG. 16 illustrates a method for implanting the implantable dialysis device 2 in a recipient 140. The recipient 140 can have a peritoneal cavity 142 and a bladder 144. The reservoir 8 can be placed in the peritoneal cavity 142, for example in the cul-de-sac of the peritoneal cavity 142. The discharge conduit 10 (e.g., the perforations 38, not shown in FIG. 16) and/or the discharge conduit port 30 can be placed in the peritoneal cavity 142. The discharge conduit 10 can be placed such that the discharge conduit first port 30 can be in fluid communication with the peritoneal cavity 142. The exit conduit 12 can be placed across the wall of the bladder 144. The anchor 44 can be placed adjacent to and/or against the outside of the bladder 144. The anchor 44 can interference fit against the outside of, or otherwise be attached to, the bladder 144. The exit port 46 can be in fluid communication with the inside of the bladder 144.

Figure 17:
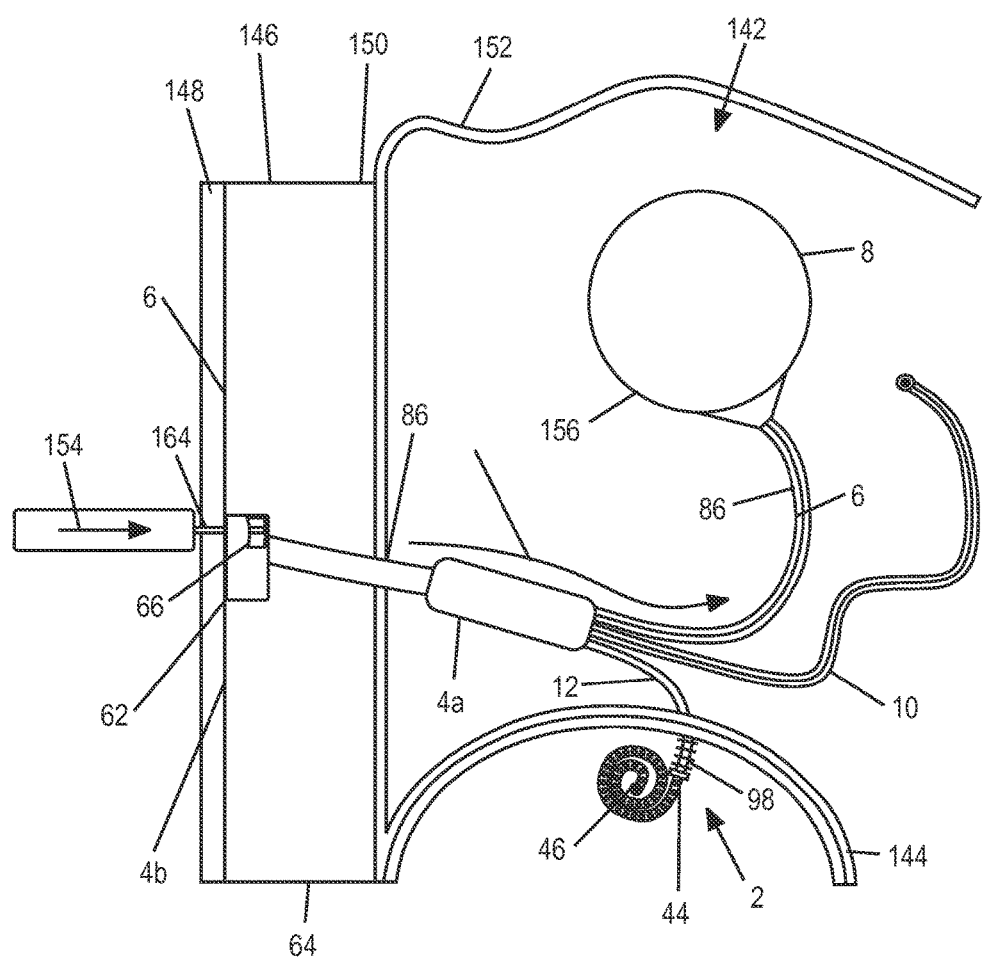
FIGS. 17-22 illustrate an embodiment of a method for peritoneal dialysis using the implantable dialysis device.

FIGS. 17 through 22 illustrate a method for performing dialysis using the implantable dialysis device 2. FIG. 17 illustrates that the second distributor 4b can be placed in a subcutaneous layer 146 between skin 148 and a muscle layer 150. The second distributor 4b can be placed directly in contact with the skin 148. The internal filling port 66 can be implanted for optimized access, for example, for access by a percutaneous injection. The first distributor 4a can be placed in the peritoneal cavity 142. The implantable dialysis device 2 can be tethered to the skin 148 and/or subcutaneous layer 146 and/or muscle layer 150 and/or peritoneal layer 152, for example, by the internal transducer connector 64 and/or part or all of the reservoir conduit 6.

The sub-anchors 98 can interference fit with the bladder 144. The sub-anchors 98 can fix the exit conduit 12 and/or the exit 14 to the bladder 144. The anchor 44 can prevent the exit 14 from moving outside of the bladder 144. The exit extension 90 can prevent the exit 14 from moving outside of the bladder 144.

A liquid, such as a solution of dialysate solute, another therapeutic or diagnostic agent, or combinations thereof, can be inserted, as shown by arrow 154, into the internal filling port 66. The liquid in the internal filling port 66 can be pumped, shown by the arrows 156, through the reservoir conduit 6 and into the reservoir 8. The liquid can be pumped, for example, through the inflow channel 86. The reservoir conduit 6 can pass through the first distributor 4a. The pump or pumps 54 (not shown) pumping the liquid to the reservoir 8 can be in the first distributor 4a an/or the second distributor 4b. The distributor valve (not shown), for example in the first distributor, can be adjusted to permit flow from the internal filling port 66 to the reservoir 8.

The reservoir 8 can be non-permeable. The reservoir conduit 6 can be non-permeable.

Figure 18:
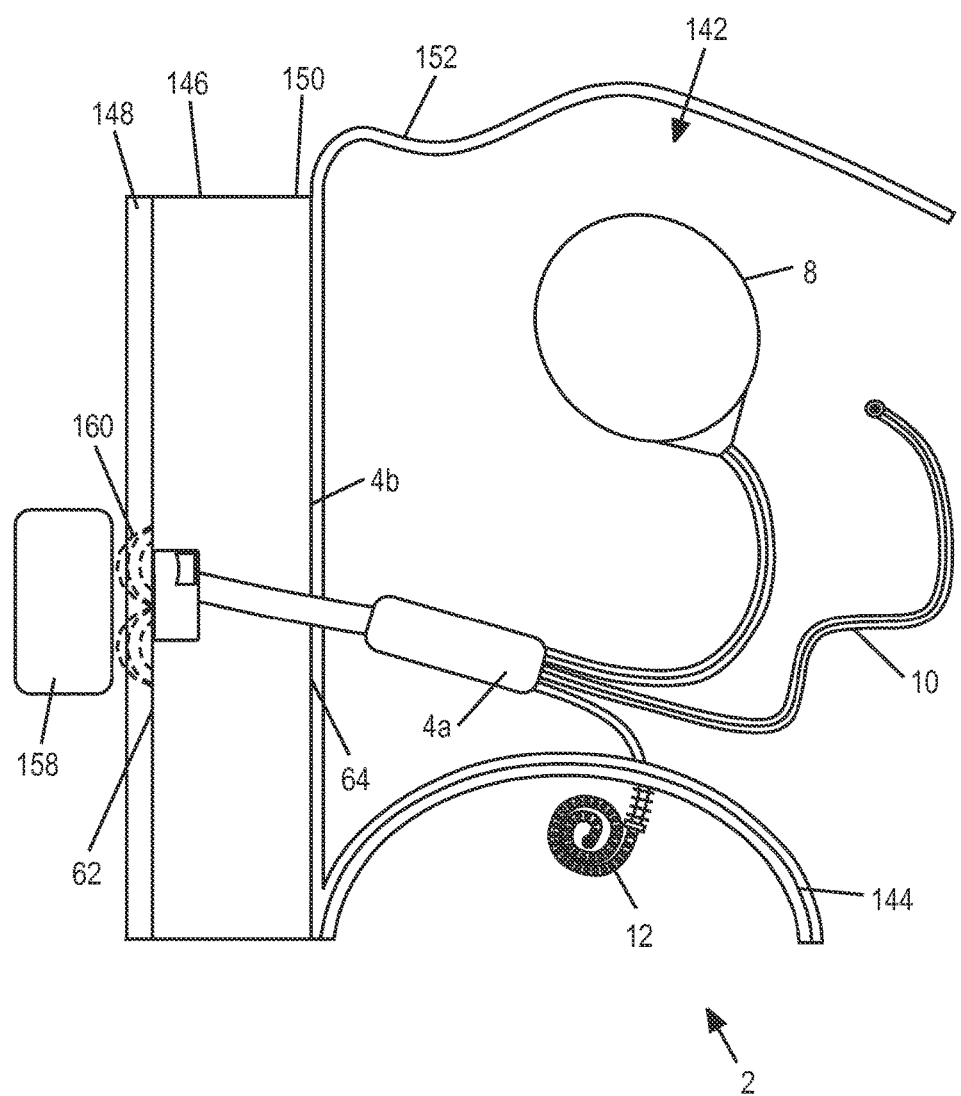

FIG. 18 illustrates that an external transducer 158 can be placed adjacent to and/or against the skin 148. The external transducer 158 can transfer energy to the internal transducer 62. The eternal transducer 158 can transmit energy waves 160. The energy waves 160 can be periodic magnetic fields. The energy waves can pass through the skin 148 and subcutaneous layer 146. The internal transducer 62 can receive the energy waves 160. The internal transducer 62 can convert the energy waves 160 into a form of energy more readily usable by the distributor. The internal transducer 62 can convert the energy waves 160 from magnetic energy into electrical energy. The internal transducer 62 can transmit energy via the internal transducer connector 64 to the pump 54 (not shown) and/or the energy storage device (not shown).

Figure 19:
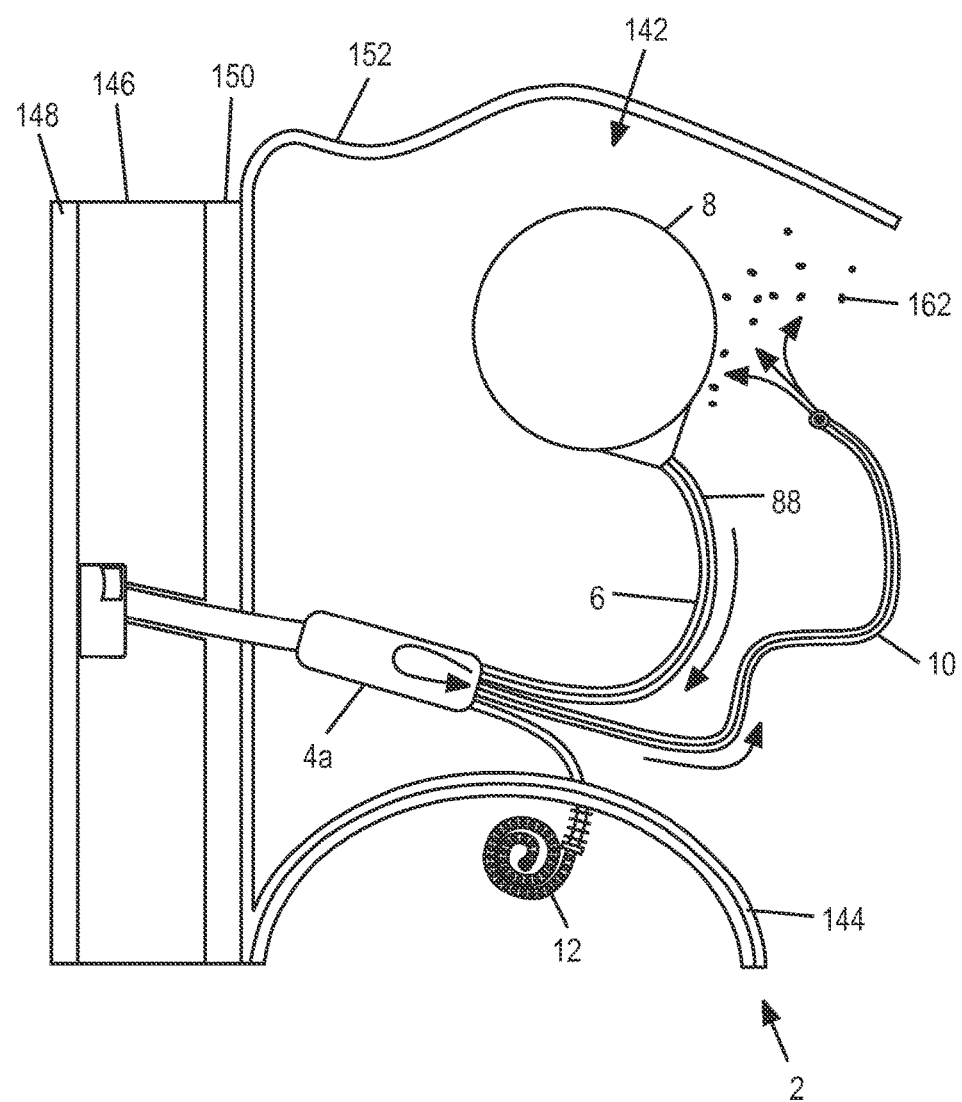

FIG. 19 illustrates that the first distributor 4a can pump, as shown by arrows, some or all of the liquid from the reservoir 8 to the peritoneal cavity 142 through the reservoir conduit 6 and the discharge conduit 10. The liquid can be pumped through the outflow channel 88. The distributor valve 56 can be adjusted to permit flow from the reservoir 8 to the peritoneal cavity 142. The liquid can contain dissolved and/or undissolved dialysate solids 162 (i.e., dialysate solute). The liquid can decrease the osmotic pressure in the peritoneal cavity 142.

Figure 20:
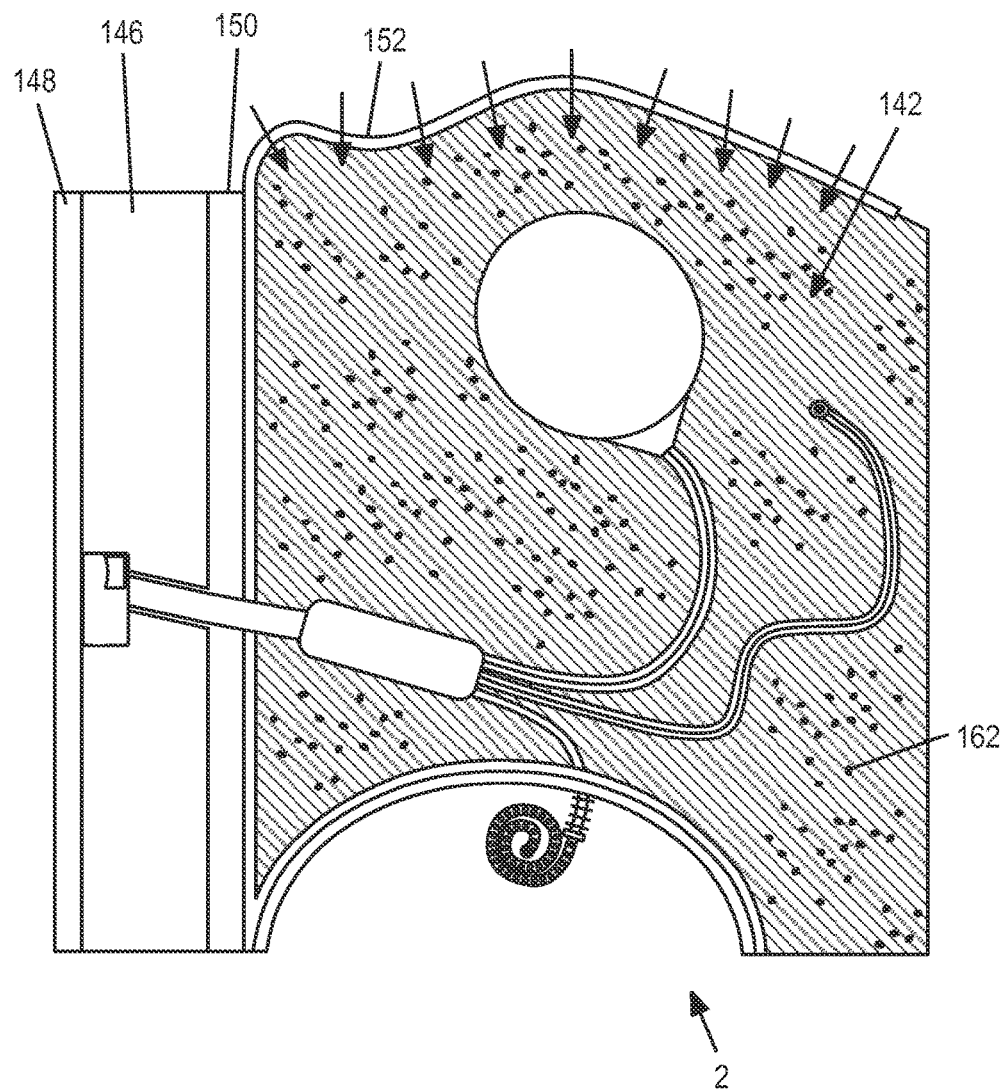

FIG. 20 illustrates that the dialysate solids 162 left in the peritoneal cavity 142 can draw, as shown by arrows, additional fluids and waste (e.g., toxins) across organ walls and the peritoneum (i.e., the peritoneal layer 152) and into the peritoneal cavity 142.

Figure 21:
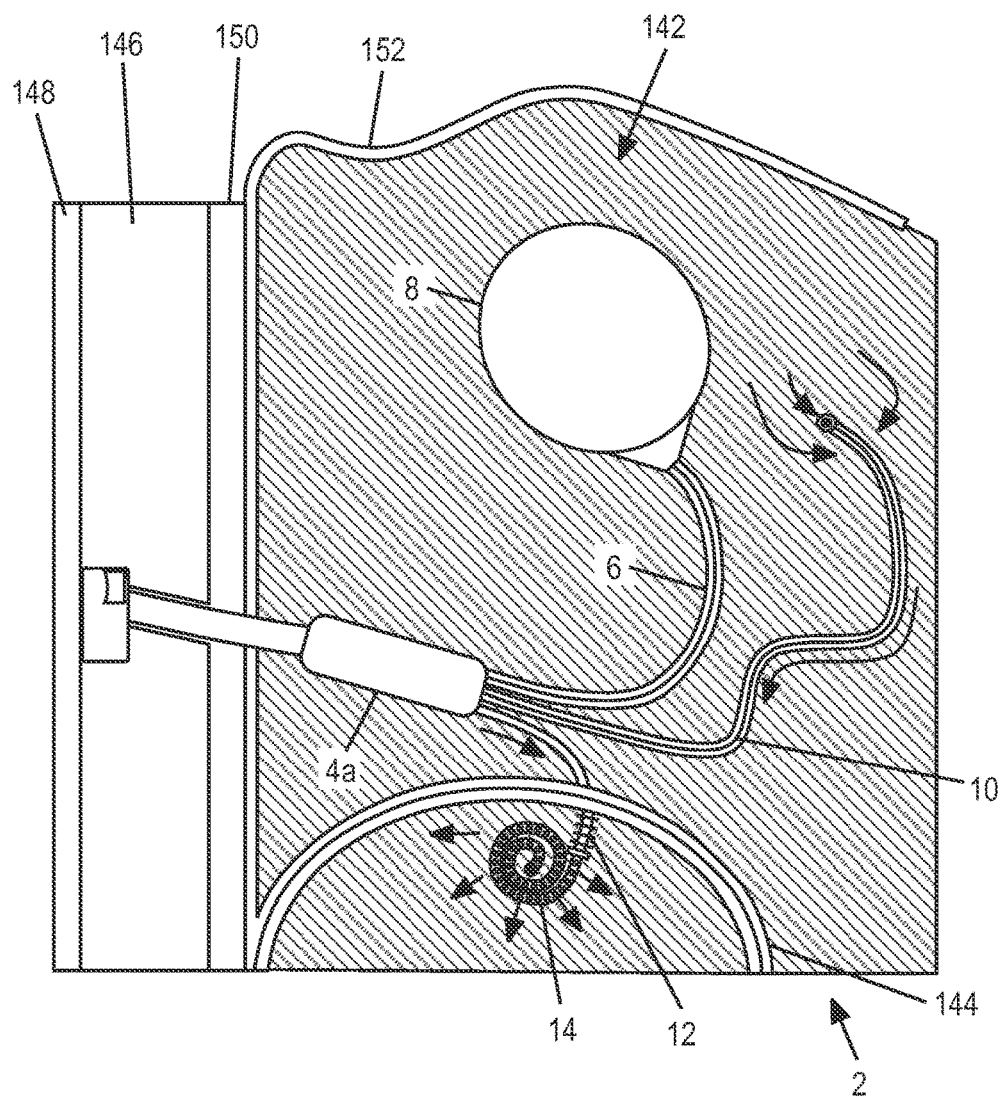

FIG. 21 illustrates that, as shown by arrows, the pump (not shown) can create pressure pulling fluids from the peritoneal cavity 142 into the discharge conduit 10, and through the exit conduit 12 into the bladder 144. The distributor valve 56 can be adjusted to permit flow from the peritoneal cavity 142 to the bladder 144. When a suitable amount of liquid and waste has been removed from the peritoneal cavity 142, the method shown in FIG. 19 can singularly or repeatedly release additional liquid from the reservoir, if more fluid is desired.

Figure 22:
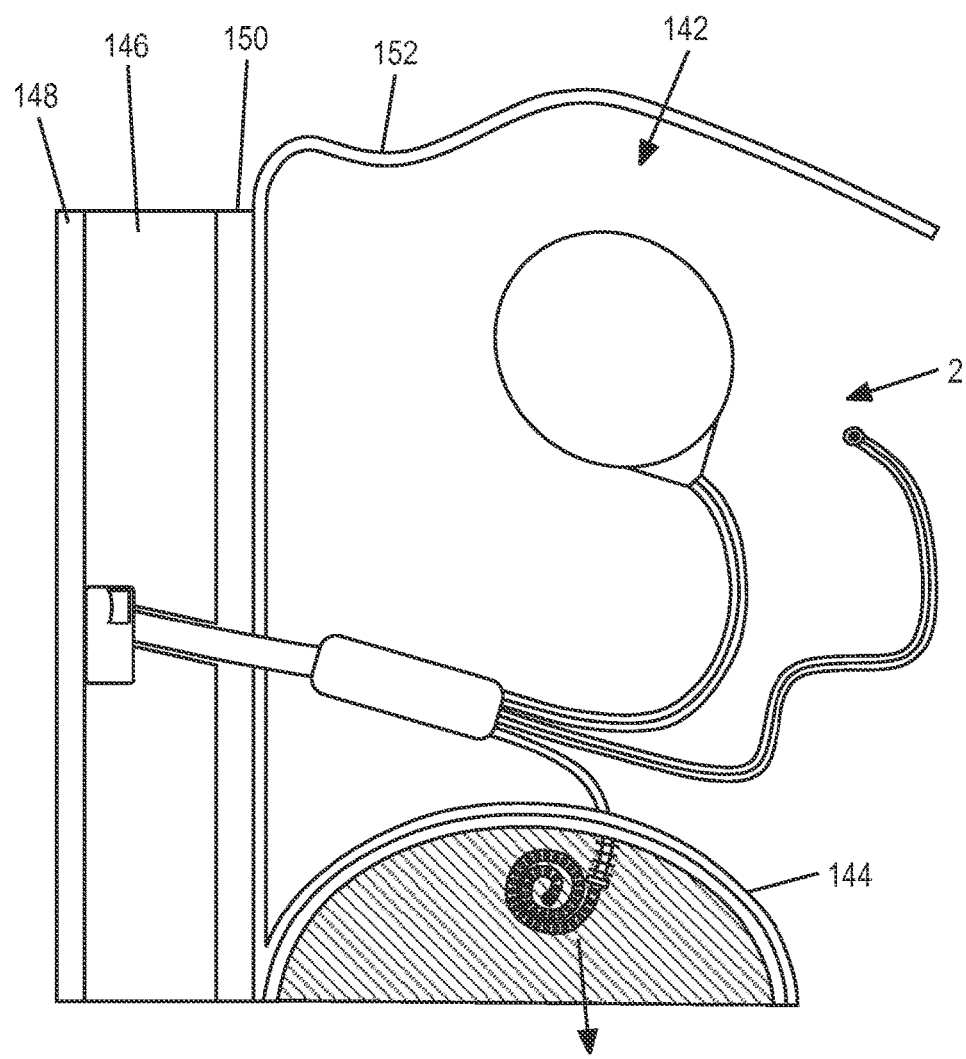

FIG. 22 illustrates that the fluid in the peritoneal cavity, for example including the waste, can be drained, as shown by arrow. The bladder can be drained with natural bladder evacuation (i.e., urination) and/or with a urethral (e.g., Foley) catheter.

The controller (not shown), for example in the first distributor 4a, can control the energy storage device. The controller can be a processor, such as a central processing unit (CPU).

The controller can communicate data with an external controller. The first component 72a can have a first controller. The second component 72b can have a second controller.

The first controller can be in data communication with the second controller. The controller can receive signals from the reservoir sensor 22, peritoneal cavity sensor 36, and bladder sensor 48 by a wire or over a data network, as described infra between controllers.

If the pressures in the peritoneal cavity 142 or the bladder 144 exceed pressure thresholds levels, the controller can stop or slow the pump 54. For example, the controller can stop or slow the pump 54 if the peritoneal pressure drops below about 11 mm Hg (0.21 psi), more narrowly below about 7 mm Hg (0.1 psi), yet more narrowly below about 4 mm Hg (0.08 psi). The controller can stop or slow the pump 54 if the absolute bladder pressure rises above about 22 mm Hg (0.43 psi), yet more narrowly above about 29 mm Hg (0.56 psi). The controller can stop or slow the pump 54 if the differential between the peritoneal and bladder pressure rises above about 15 mm Hg (0.29 psi), more narrowly above about 22 mm Hg (0.43 psi).

The controller can stop the pump 54 and/or adjust the distributor valve 56 to release the excess pressure (e.g., from the peritoneal cavity into the bladder).

The controller can control the distributor 4, for example including the pump 54 and/or the distributor valve 56. The controller can monitor the quantity and/or quality (e.g., ratio of dialysate solute volume to solvent or solution volume, solution temperature) of stored liquid in the implantable dialysis device 2. The controller can regulate valve adjustments. The controller can regulate the distribution of fluids and solutes by the implantable dialysis device 2. The controller can have a clock. The controller can control the implantable dialysis device based on the clock. For example, the controller can be programmed to deliver about 100 mL (6 in.$^3$) of dialysate solution from the reservoir 8 into the peritoneal cavity 142 for one-hour of every six hours.

When the implantable dialysis device 2 is low or out of stored liquid or dialysate solute, the controller can create, for example, through the distributor, a vibration or other signal to indicate that the implantable liquid or dialysis device 2 is low or out of stored dialysate solute.

FIGS. 23 through 27 illustrate a method for performing dialysis using the implantable dialysis device 2. The distributor 4 can be placed in the subcutaneous layer 146 adjacent to and/or against the muscle layer 150. The internal transducer 62 can be placed in the subcutaneous layer 146 adjacent to and/or against the skin 148. The discharge conduit first port 30 and the drainage conduit first port 75 can be in the peritoneal cavity 142.

Figure 23:
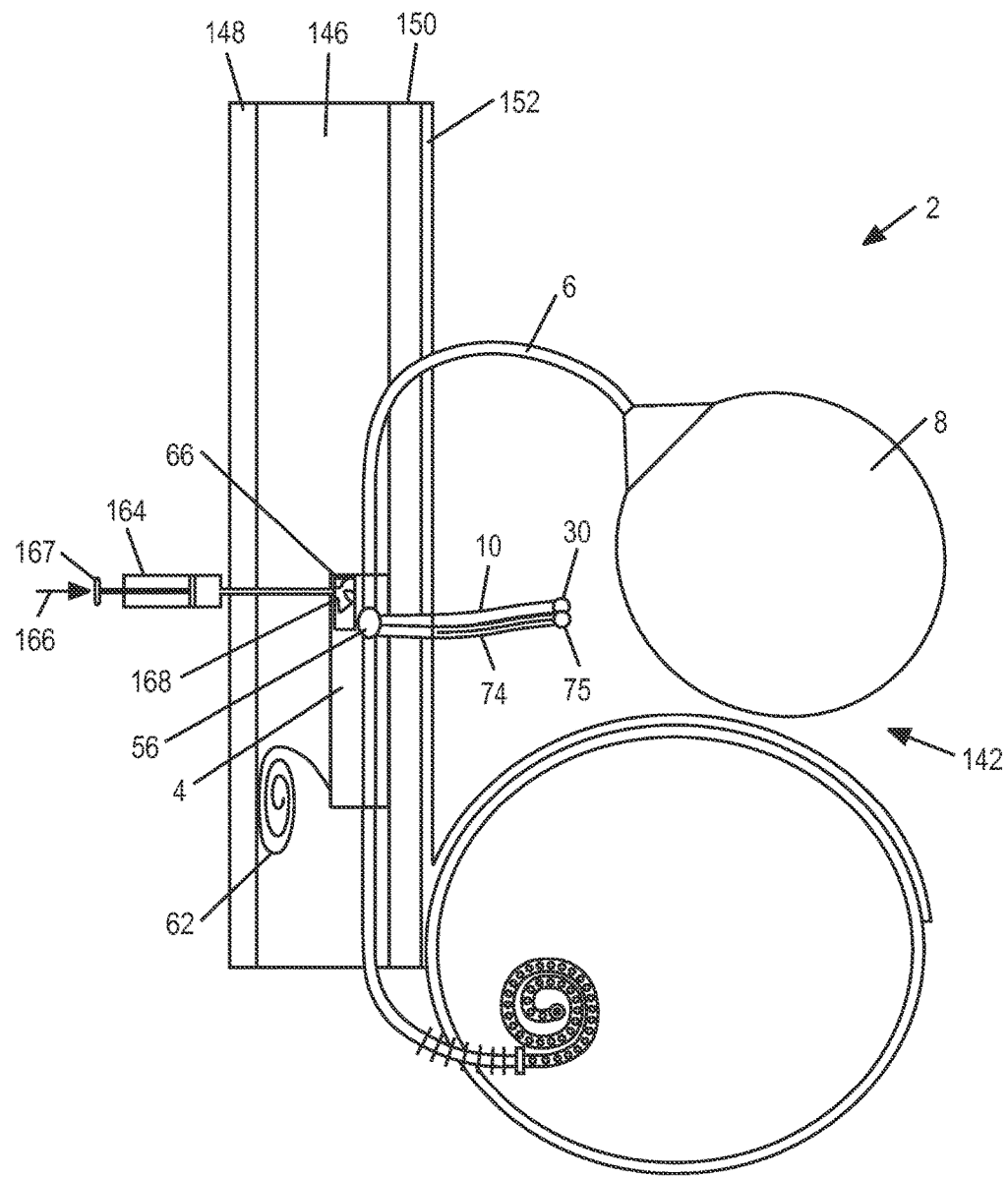
FIGS. 23-27 illustrate an embodiment of a method for peritoneal dialysis using the implantable dialysis device.

FIG. 23 illustrates that a needle and syringe 164 can be injected into the internal filling port 66. The syringe can hold liquid. Pressure can be applied, as shown by arrow 166, to a plunger 167 on the syringe 164. The liquid can then enter, as shown by arrow 168, the internal filling port. The distributor valve 56 can be configured so the liquid can controllably flow out of the internal filling port 66.

Figure 24:
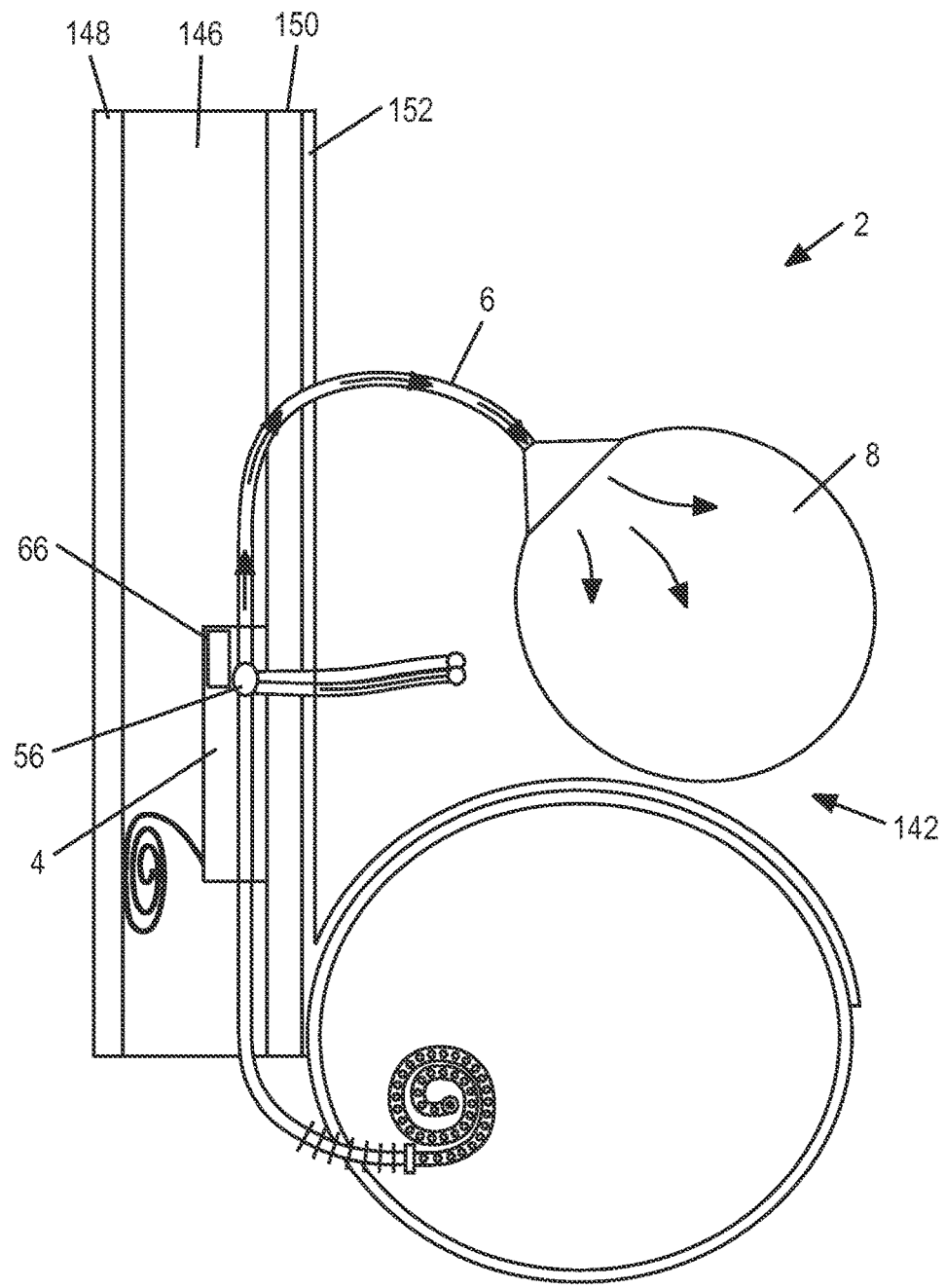

FIG. 24 illustrates that the liquid is the internal filling port 66 can be pumped, shown by the arrows, by the distributor 4 to the reservoir 8. The distributor valve 56 can be adjusted to permit flow from the internal filling port 66 to the reservoir 8. The reservoir 8 can then hold the liquid. The pump (not shown) can be powered using one or more methods described supra. When the distributor 4 has completed pumping liquid to the reservoir conduit 6 and/or the reservoir 8, the distributor valve 56 can be adjusted to prevent flow out of the reservoir conduit 6 to or through the distributor 4.

Figure 25:
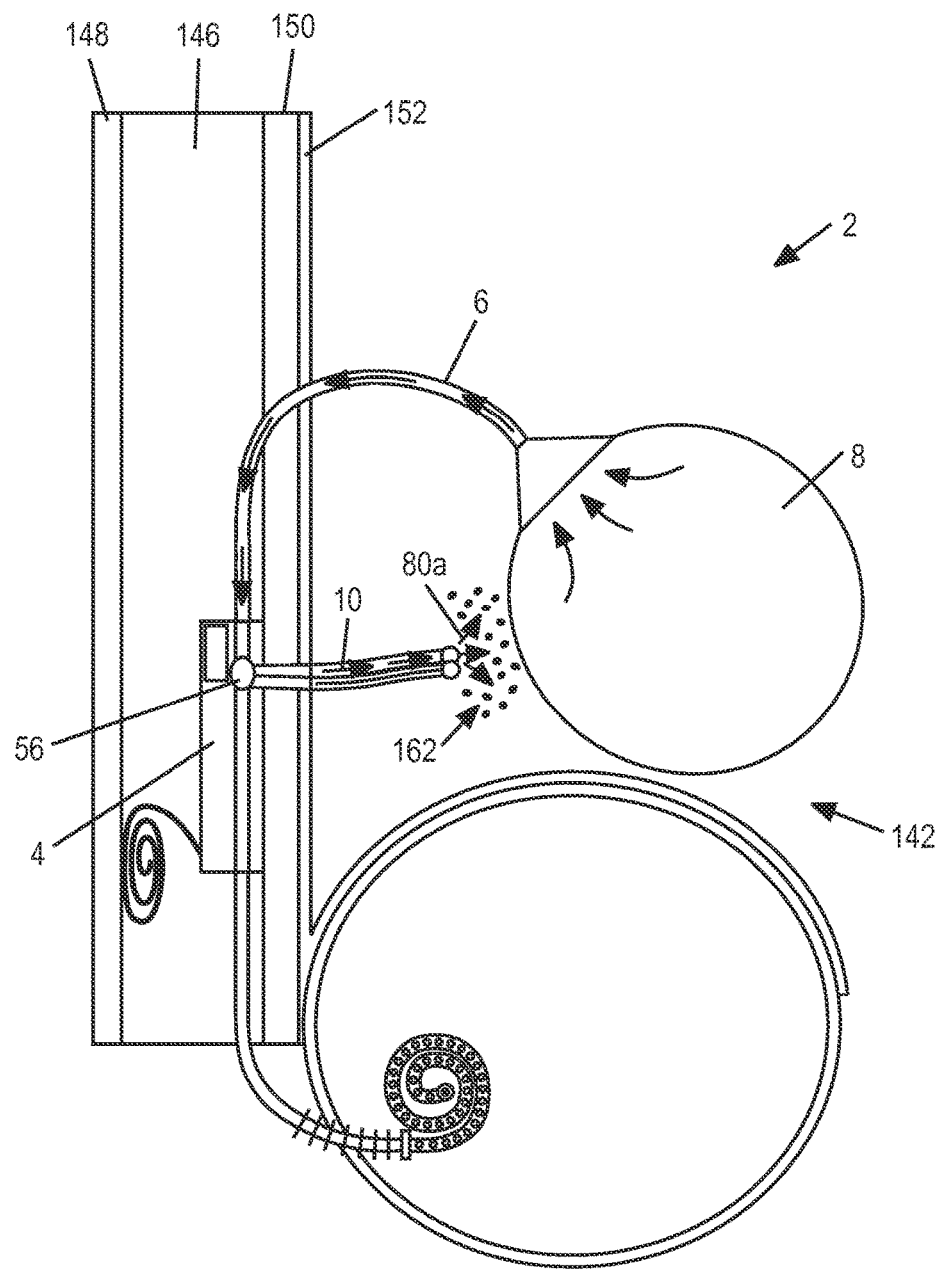

FIG. 25 illustrates that, when appropriate, the distributor 4 can pump, as shown by arrows, some or all of the liquid from the reservoir 8 to the peritoneal cavity 142, for example, via the discharge conduit 10. The distributor valve 56 can be adjusted to permit flow from the reservoir 8 to the discharge conduit 10. The liquid can be enter the peritoneal cavity 142. The liquid can have dialysate solids 162. The liquid can decrease the osmotic pressure in the peritoneal cavity 142.

Figure 26:
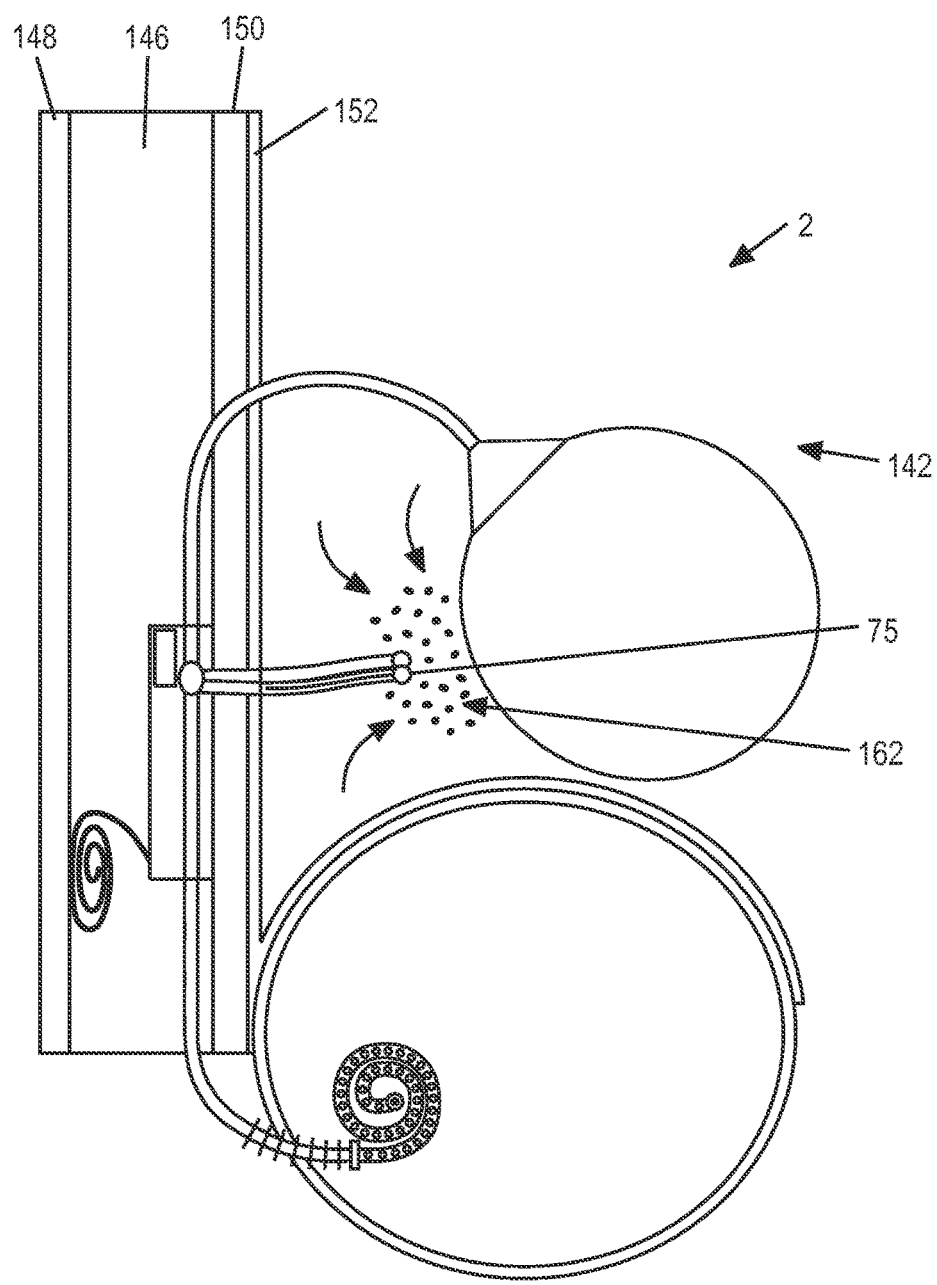

FIG. 26 illustrates that dialysate solids 162 left in the peritoneal cavity 142 can draw, as shown by arrows, additional fluids and waste across organ walls and the peritoneum and into the peritoneal cavity 142. The additional fluids can increase the fluid pressure in the peritoneal cavity 142.

Figure 27:
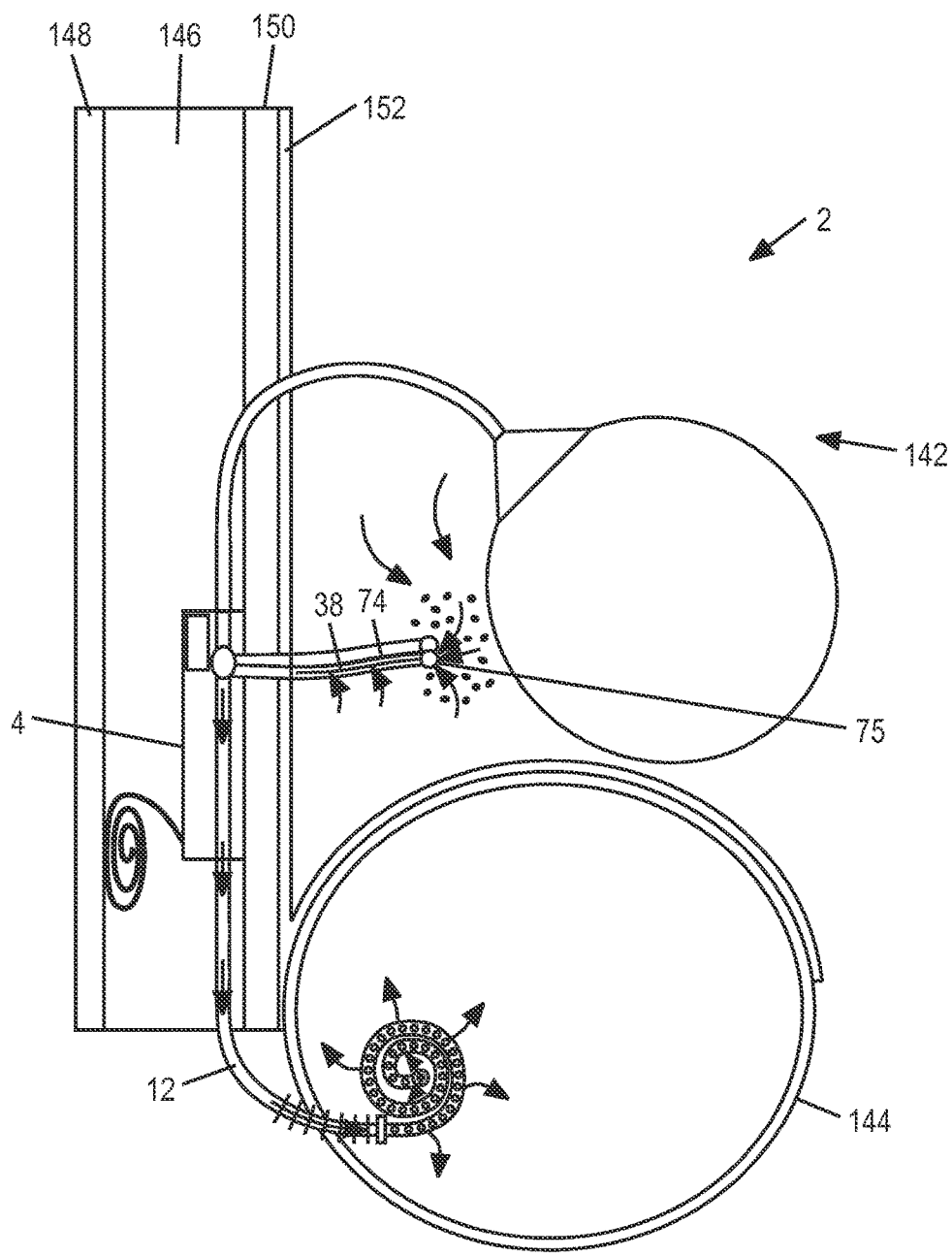

FIG. 27 illustrates that fluids in the peritoneal cavity 142 can be evacuated by the peritoneal dialysis device 2. The distributor valve 56 can permit flow from the drainage conduit 74 to the exit conduit 12. As shown by arrows, the pump (not shown) can create pressure pulling fluids from the peritoneal cavity 142 into the drainage conduit 74, and through the exit conduit 12 into the bladder 144. The patient can dispose of fluids in the bladder 144 through urination or a catheter. Fluids can enter the drainage conduit 74 through the perforations 38, and/or the drainage conduit first port 75, and/or the second discharge conduit first port guard 80*a*.

Figure 28:
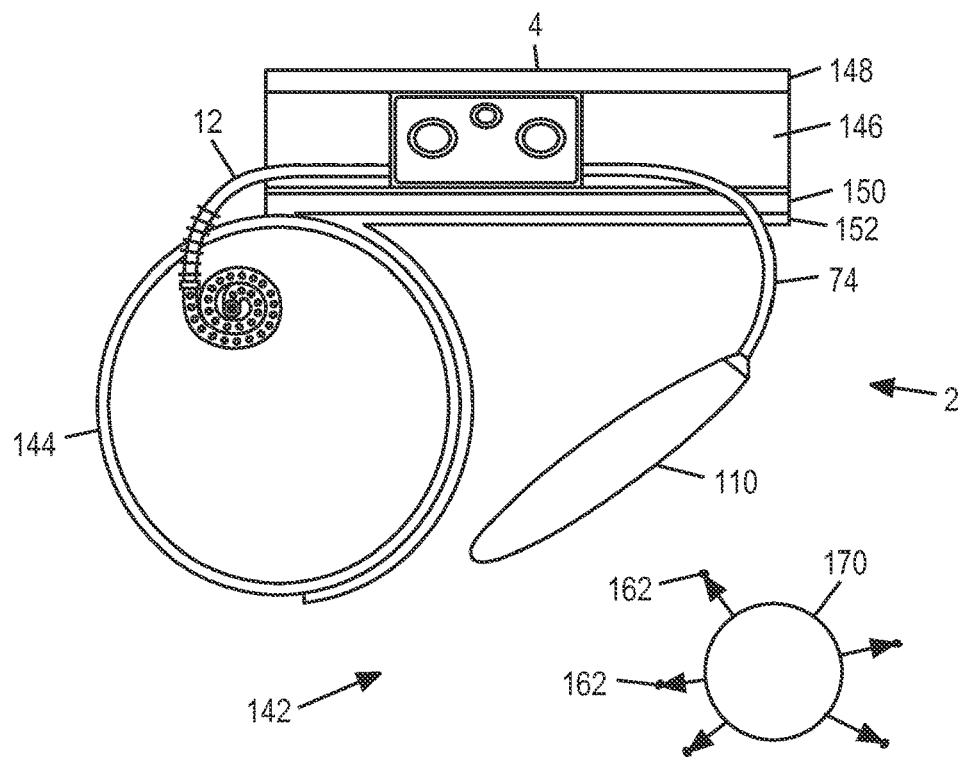
FIGS. 28-32 illustrate various embodiments of a method for peritoneal dialysis using the implantable dialysis device.
Figure 29:
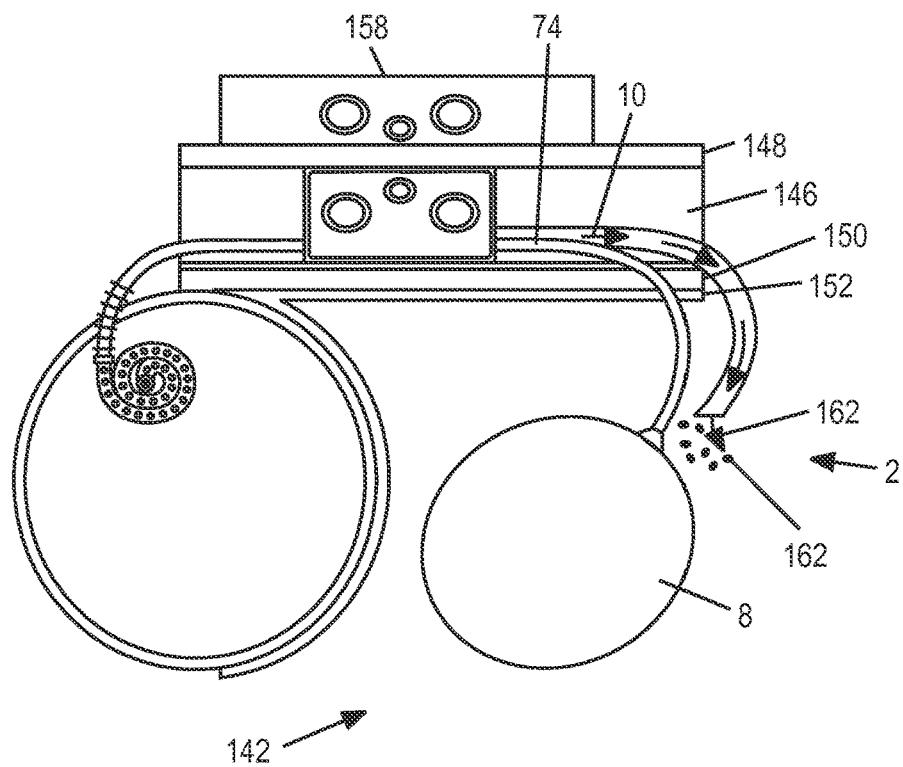

FIGS. 28 through 32 illustrate various methods for performing dialysis using the implantable dialysis device 2 having the transfer element 110. FIGS. 28 and 29 illustrate various methods for introducing dialysate solids into the peritoneal cavity 142. The transfer element 110 can be resiliently biased in an expanded configuration.

FIG. 28 illustrates that a dialysate implant 170 can be placed in the peritoneal cavity 142. The dialysate implant 170 can elute dialysate solids 162 in the peritoneal cavity 142.

The dialysate implant 170 can be a solution, a gel matrix with dialysate solids, a polymer matrix with dialysate solids, made wholly of dialysate solid or combinations thereof. The gel matrix with dialysate solids, polymer matrix with dialysate solids, wholly dialysate solid, or combinations thereof can be formulated to time-release dialysate solids. The dialysate implant 170 can be made from alginate cross-linked with calcium.

The dialysate solids can be any dialysate solutes out of solution. The dialysate solids can be, for example bicarbonate, dextrose, glucose, sodium, sodium chloride, sodium lactate, calcium chloride, magnesium chloride, citric acid, one or combinations of glucose (e.g., about 2.27% solution, MW of about 180.16), maltose, such as maltose disaccharide (e.g., about 4.32% solution, MW of about 342.30), maltotriose, such as maltotriose trisaccharide (e.g., about 6.36% solution, MW of about 504.44), maltopentaose, such as maltopentaose pentasaccharide (e.g., about 10.4% solution, MW of about 828.72), Icodextran and/or any other osmotically active material or combinations thereof.

FIG. 29 illustrates that the distributor 4 can pump, as shown by arrows, the contents of the internal filling port 66 to the peritoneal cavity 142. The external transducer 158 and/or an energy storage device in the implantable dialysis device 2 can provide the energy to pump. Placing the dialysate implant 170 in the peritoneal cavity 142, as shown in FIG. 28, can be performed alone or in combination with pumping the contents of the internal filling port 66 to the peritoneal cavity 142 (as shown in FIG. 29) and/or to the reservoir 8.

If the dialysate solids or solutes are introduced into the peritoneal cavity 142, the osmotic pressure in the peritoneal cavity can decrease, thereby drawing fluid, and the associate waste, from the vascular system and the adjacent organs into the peritoneal cavity 142. The fluid pressure in the peritoneal cavity 142 can increase. A pressure gradient across the surface of the reservoir 8 can force fluid from the peritoneal cavity 142 into the reservoir 8. The resiliency of the reservoir 8 can keep the reservoir in an expanded configuration when the pressure in the peritoneal cavity increases, thereby potentially creating a larger pressure gradient across the surface of the reservoir 8 and potentially increasing the fluid flow rate across the surface of the reservoir 8.

Figure 30:
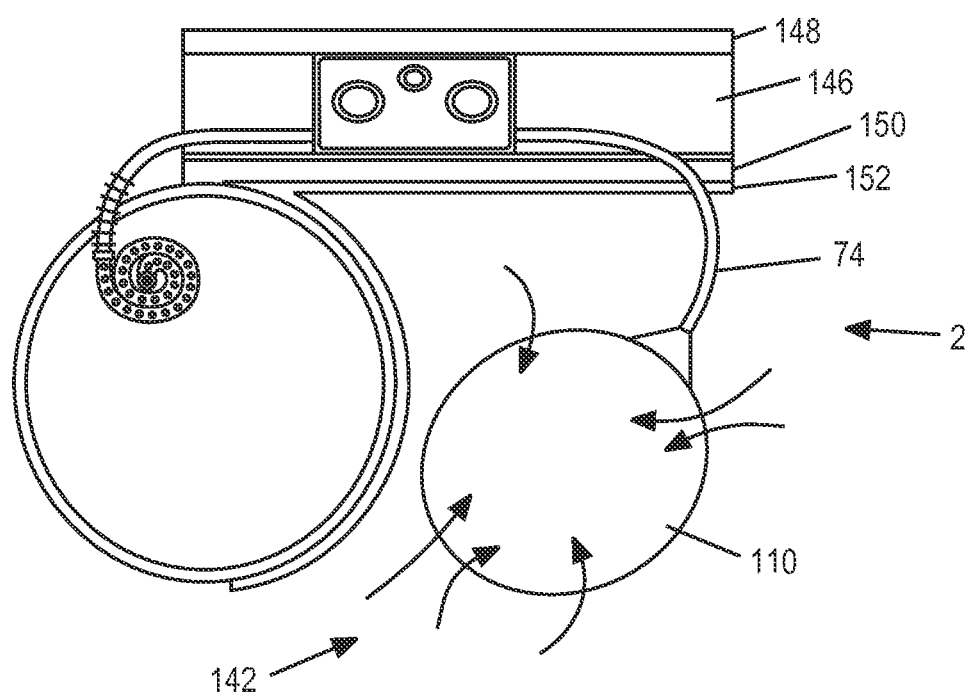
Figure 31:
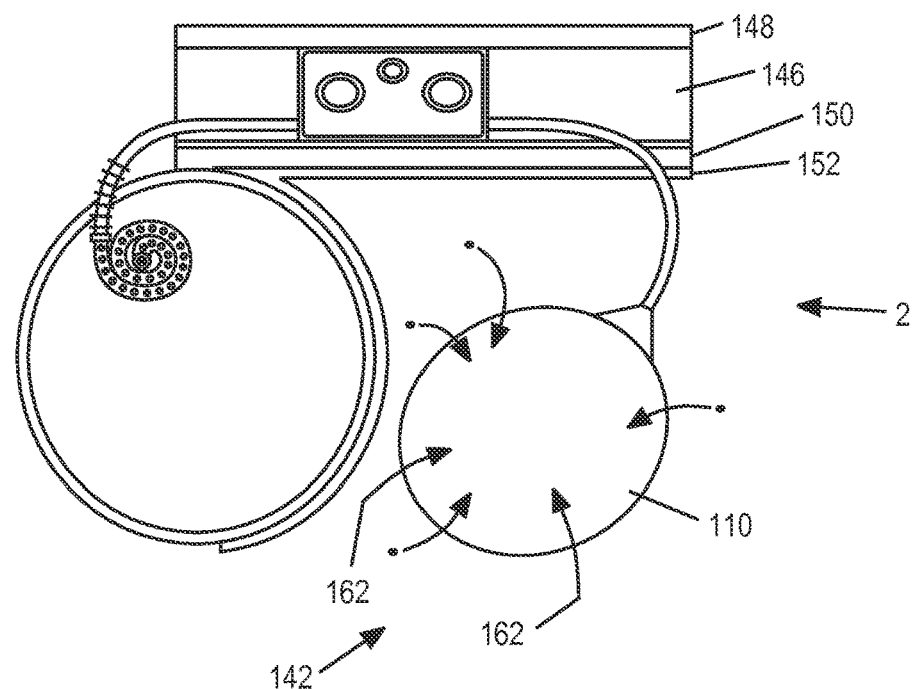

FIG. 30 illustrates that fluid in the peritoneal cavity can permeate, as shown by arrows, into the transfer element 110. When fluid permeates into the transfer element 110, the transfer element 110 can expand. FIG. 31 illustrates that particles, for example small solutes, such as urea and creatinine, can permeate, as shown by arrows, into the transfer element 110. Particles, such as proteins, can be filtered from entering the transfer element 110 based on particle size and/or particle charge.

The fluid, as shown in FIG. 30, and the particles, as shown in FIG. 31, can concurrently permeate the transfer element 110, for example across the transfer element face 112. The transfer element 110 can fill with a waste fluid, and, if used, dialysate solids and/or solution.

Figure 32:
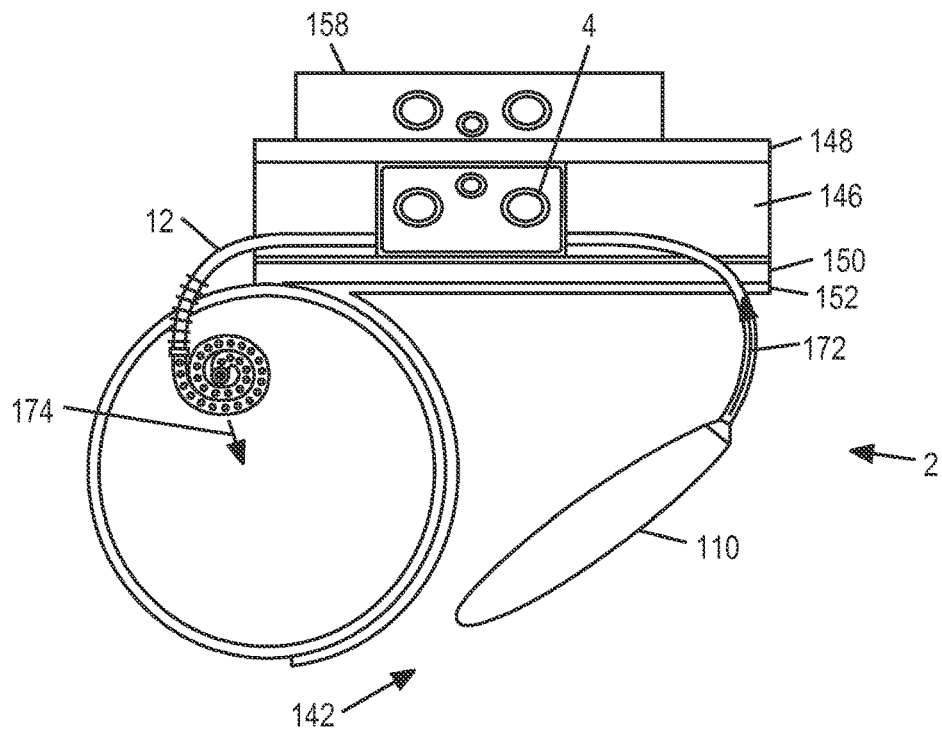

FIG. 32 illustrates that the distributor 4 can pump, as shown by arrow 172, the waste fluid out of the reservoir 8. When the waste fluid is pumped out of the transfer element 110, the transfer element 110 can remain resiliently in an expanded configuration. When the waste fluid is pumped out of the transfer element 110, the transfer element 110 can resiliently contract. The distributor 4 can pump the waste fluid through the discharge conduit 10. The distributor 4 can pump the waste fluid through the distributor 4. The distributor 4 can pump the waste fluid through the exit conduit 12. The distributor 4 can pump the waste fluid through the exit 14. The waste fluid can be pumped, as shown by arrow 174, or otherwise flow, into the bladder 144.

The transfer element 110 can be continuous emptied of waste fluids and solids by the distributor 4. The transfer element 110 can be emptied of fluid by the distributor 4, then the distributor 4 can wait until the transfer element 110 accumulates a minimum quantity or pressure of fluid before the distributor 4 again empties the transfer element 110 of fluids and solids.

Figure 33:
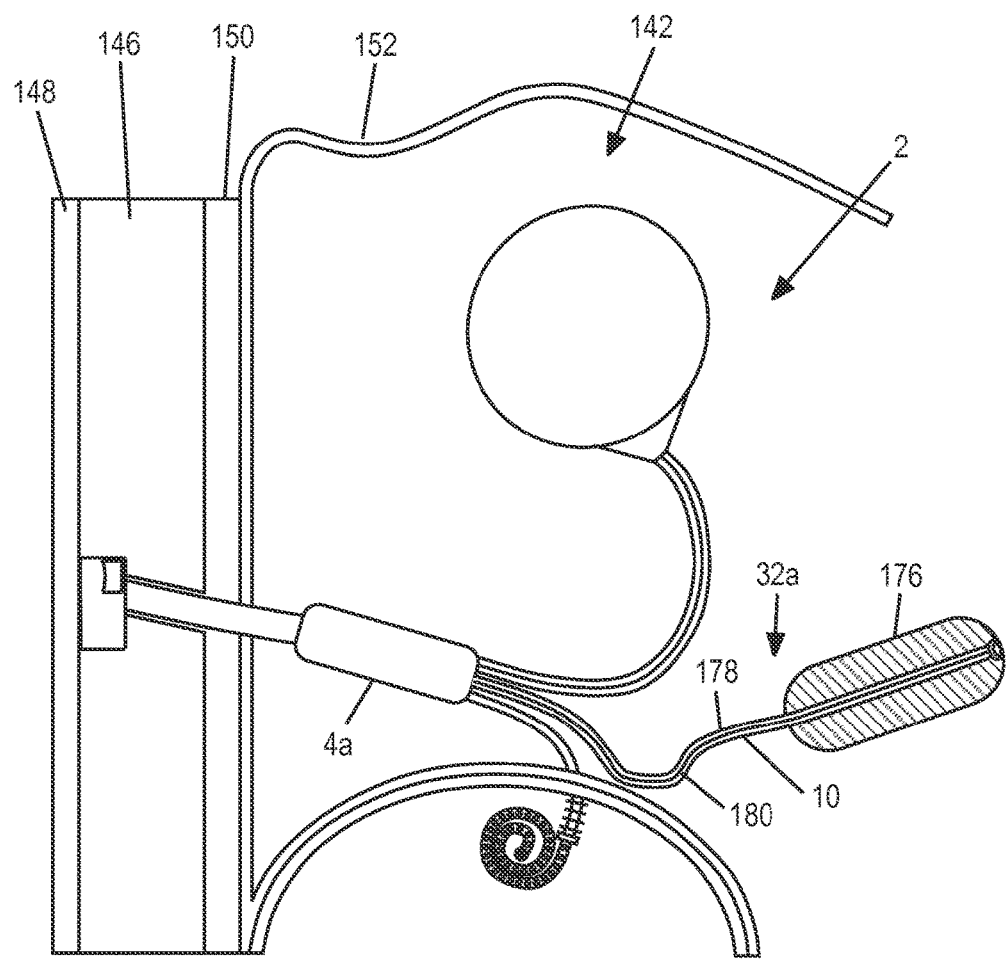
FIG. 33 illustrates an embodiment of a method for using the implantable dialysis device having a mixing chamber.

FIG. 33 illustrates a method for using the implantable dialysis device with a mixing chamber 176. The discharge conduit 10 can have a pre-mix channel 178 and a drainage channel 180. The mixing chamber 176 can be attached to the discharge conduit first end 32*a*. The mixing chamber 176 can be configured to mix peritoneal fluid with the dialysate or other liquid before the liquid flows from the discharge conduit 10 to the peritoneal cavity 142. The mixing chamber 176 can be a perforated or non-perforated chamber. The mixing chamber 176 can draw peritoneal fluid into the mixing chamber. The mixing chamber 176 can then mix the peritoneal fluid with the liquid (e.g., concentrated dialysate) prior to release into the peritoneal cavity 142. The mixing chamber 176 can be separate from the discharge conduit 10 and/or drainage conduit 74. The mixing chamber 176 can also prevent trapping the bowel or other peritoneal contents in the discharge conduit first port 30.

If the dialysate solution is mixed with peritoneal fluid to reduce the solute-to-solvent ratio of the fluid before the fluid enters the peritoneal cavity 142, the dialysate solution can be held in the reservoir 8 to allow for dilution of the solute prior to release into the peritoneal cavity. The discharge conduit 10 can have the pre-mix channel 178 and the drainage channel 180.

Figure 34:
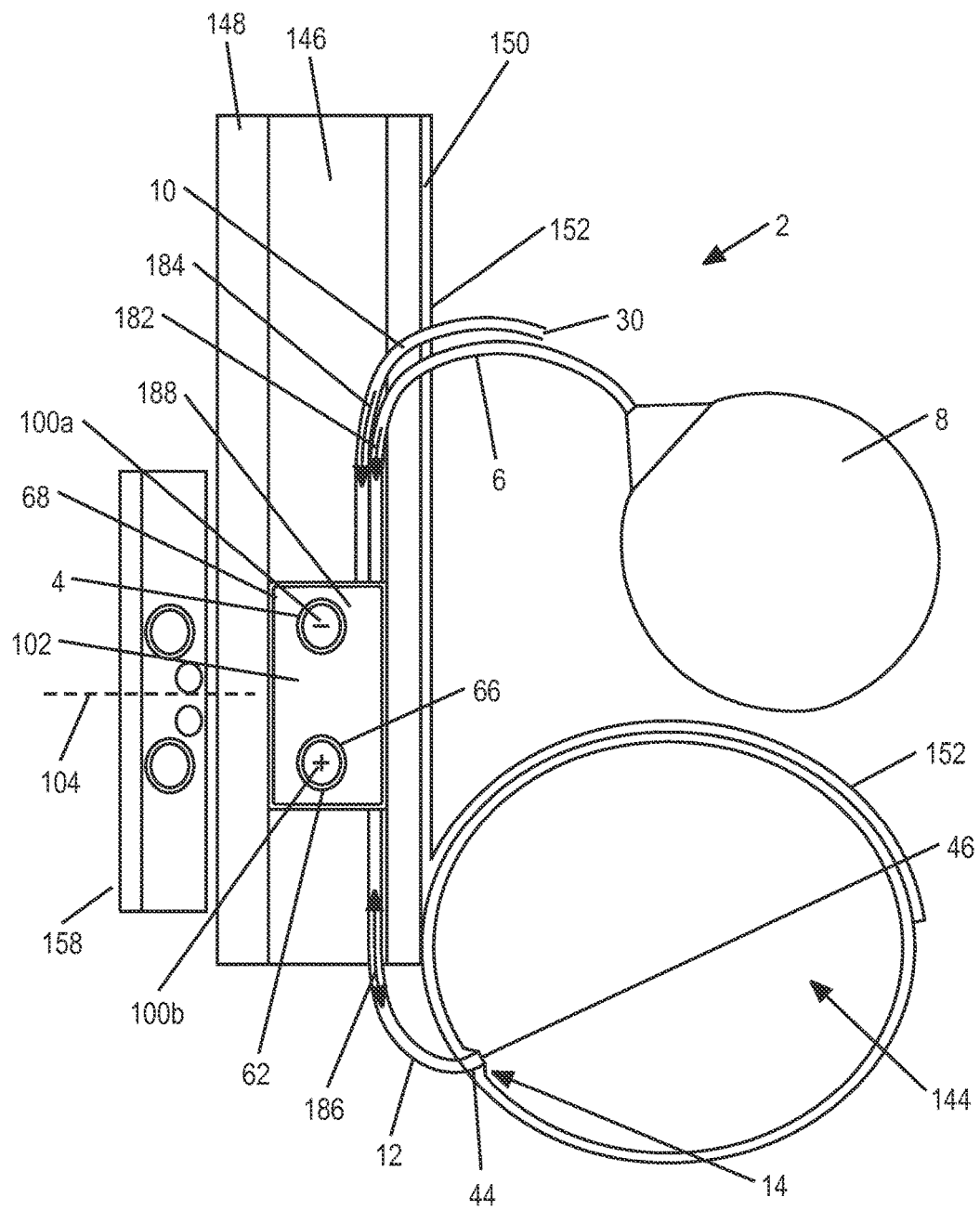
FIG. 34 illustrates an embodiment of a method for using the implantable dialysis device having a inductive dipole transducer.

FIG. 34 illustrates that the internal transducer can have first and second first and second magnetic poles 100*a* and 100*b*. The pole axle 102 can attach the first pole 100*a* to the second pole 100*b*. The pole axle 102 can be configured to rotate about the motor rotation axis 104 or be otherwise attached (e.g., via a geared transmission, driveshaft, or combinations thereof) to mechanically transmit rotational force to the motor rotation axis 104. The external transducer 158 can have rotational poles offset from the first and second poles 100*a* and 100*b* of the internal transducer 62 (e.g., the negative pole in the external transducer 158 can align with the positive pole of the internal transducer 62).

If the poles in the external transducer 158 are rotated about the motor rotation axis 104, the first and second poles 100*a* and 100*b* of the internal transducer 62 can exert a rotational force about the motor rotation axis 104 on the pole axle 102. The pole axle 102 can rotate about the motor rotation axis 104. The pole axle 102 can drive the flow driving mechanism (e.g., a crankshaft on the pump 54).

The pump 54 can drive, as shown by arrows 182, fluid flow in the reservoir conduit 6 to or from the reservoir 8. The pump 54 can drive, as shown by arrows 184, fluid flow in the discharge conduit 10 from the reservoir 8 or to the distributor 4. The pump 54 can drive, as shown by arrows 186, fluid flow at the exit conduit 12 to the exit 14 from the distributor 4. The pump 54 can drive, as shown by arrows 188, fluid flow in the internal filling port 66 to the reservoir conduit 6 or the discharge conduit 10. Fluid flow can be driven by dynamic mechanical pressure or by osmotic pressure gradients.

Figure 35:
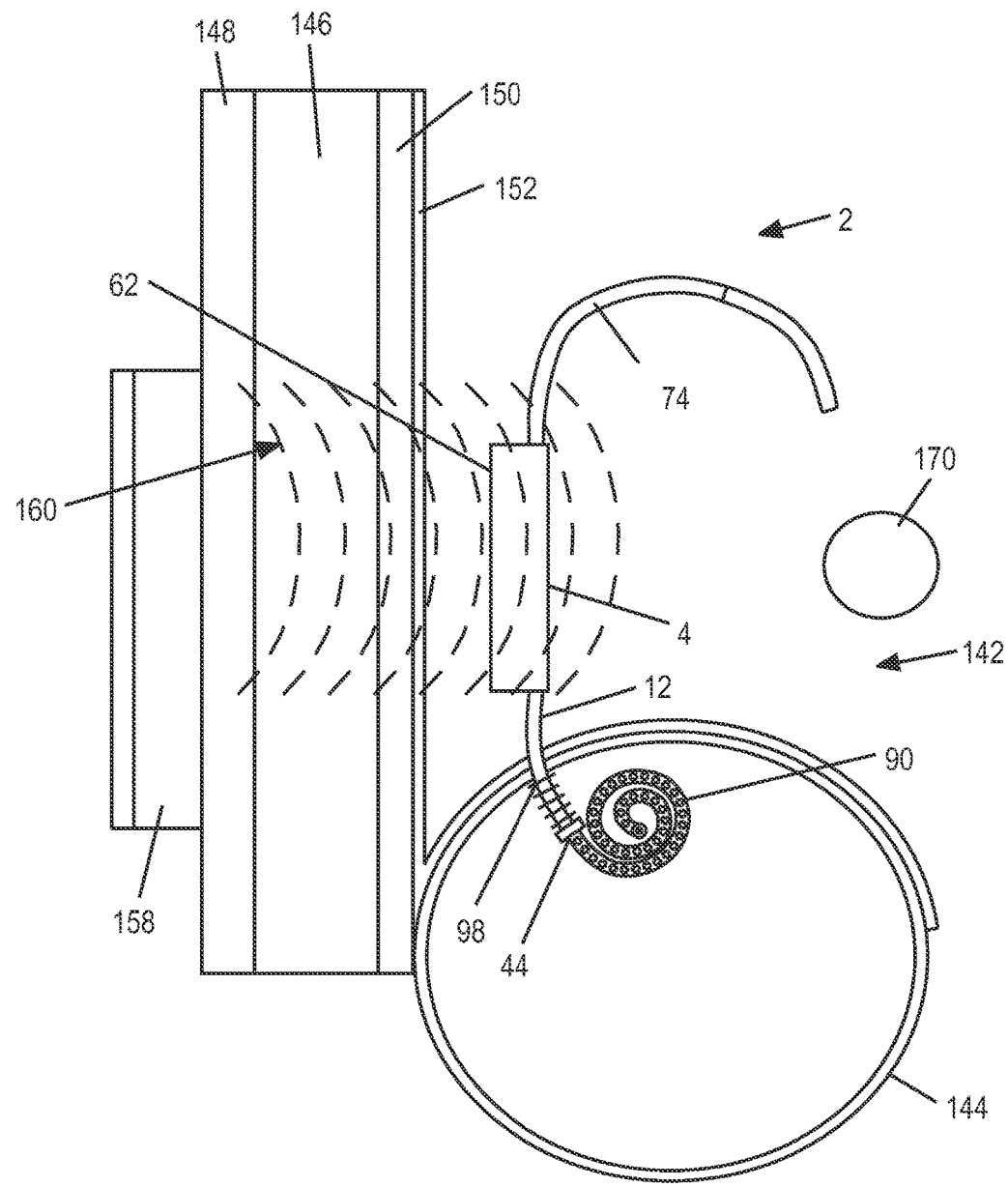
FIG. 35 illustrates an embodiment of a method for using the implantable dialysis device implanted wholly in the peritoneal cavity and the bladder.

FIG. 35 illustrates that the distributor 4 can be placed wholly in the peritoneal cavity 142. The external transducer 158 can transmit energy waves 160 into the peritoneal cavity 142. The external transducer 62 can receive the energy waves 160. The drainage conduit 74 can be wholly within the peritoneal cavity 142.

Figure 36:
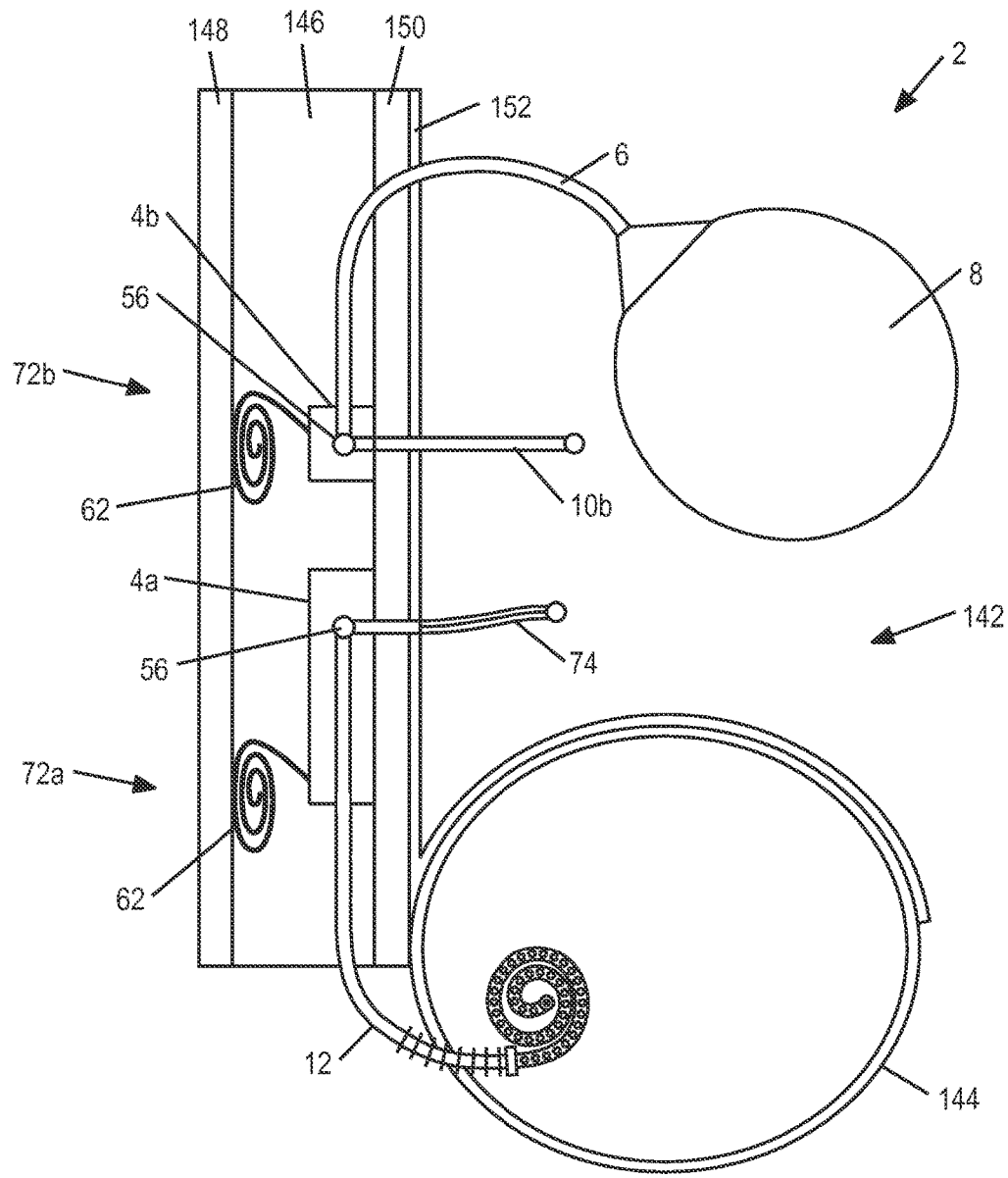
FIG. 36 illustrates an embodiment of a method for using the implantable dialysis device with a first component and a second component.

FIG. 36 illustrates the implantable dialysis device 2 that can have the first component 72*a* and the second component 72*b*. The first component 72*a* can be placed at a distance away from the second component 72*b*. The first and/or second components 72*a* and/or 72*b* can have a distinct and separate internal transducer 62.

For any embodiment of the implantable dialysis device 2, the port guards 80 can prevent the discharge conduit ports 30, or other ports (e.g., drainage conduit ports 75) from being blocked by solid objects (e.g., organs and/or the dialysate implant 170), for example, in the peritoneal cavity 142.

The distributor 4 can have or otherwise be in contact with the battery 60, capacitor or other energy storage device (not shown). The external transducer 158 can charge the energy storage device, for example, via the internal transducer 62. The energy storage device can be used to power the distributor 4 and/or other components of the implantable dialysis device 2. When the energy storage device is low on stored power, a vibration or other signal, for example from the distributor, can be created to indicate that the energy storage device is low on power.

The patient can manually control the distributor 4, for example with the external transducer 158, and/or the controller can control the internal transducer 62. When the pressures, or other characteristics, sensed by the reservoir sensor 22, peritoneal cavity sensor 36 and/or bladder sensor 48, are out of a predetermined range, the controller can create, for example, through the distributor, a vibration or other signal to indicate that the pressures, or other characteristics, are out of a predetermined range, and/or control, for example by stopping, the pump 54 and distributor valve 56. The controller can shut-off the pump 54, and/or override manual control, when the bladder sensor 48 reports a bladder pressure, or other characteristic, above or below a predetermined safe level. The controller can activate the pump 54, and/or override manual control, when the reservoir sensor 22 reports a reservoir pressure, or other characteristic, above or below a predetermined safe level.

A cleaning fluid, for example saline solution, can be injected, for example under high pressure, into the reservoir 8 and/or transfer element 110, for example directly into the transfer element 110 and/or via the distributor 4 and/or the discharge conduit 10. The cleaning fluid can exit the transfer element 110 into the peritoneal cavity 142. The cleaning fluid can backwash the transfer element 110. The cleaning fluid can dislodge particles, for example proteins, in the pores of the transfer element 110.

The implantable dialysis device 2 can be used to treat and prevent congestive heart failure (CHF) and high blood pressure. By draining fluid from the peritoneal cavity 142, and thereby reducing the fluid pressure in the peritoneal cavity 142, the implantable dialysis device 2 can induce venous fluid loss into the peritoneal cavity 142. This induction of venous fluid loss into the peritoneal cavity 142 can reduce venous pressure, and prevent or minimize venous fluid release in the lungs. Regardless of disease state being treated, the patient can maintain hydration after implantation of the implantable dialysis device 2 by drinking fluids or otherwise receiving supplemental intravenous fluids.

It is apparent to one skilled in the art that various changes and modifications can be made to this disclosure, and equivalents employed, without departing from the spirit and scope of the invention. Elements shown with any embodiment are exemplary for the specific embodiment and can be used on other embodiments within this disclosure. Some elements have been omitted from some figures for clarity of illustration, but the omission of these elements does not constitute lack of written disclosure of the use of these elements with the embodiments shown in the figures in which these elements are not shown.

Furthermore, use of delineating nomenclature (e.g., first, second) is not intended to be limiting. For example, designs and methods of use described for the first and second distributors 4a and 4b can be used for the distributor 4 and vice versa.

We claim:

1. A fluid management system comprising:
    an infusate comprising an osmotic agent for infusion into a peritoneal cavity;
    a reservoir conduit adapted for introducing the infusate into the peritoneal cavity;
    an implantable pump having an internal battery that is inductively chargeable, the implantable pump adapted for fluidic communication with the peritoneal cavity and a bladder;
    a drainage conduit adapted for coupling between the peritoneal cavity and the implantable pump; and
    an exit conduit adapted for coupling between the bladder and the implantable pump,
    wherein the implantable pump is configured to pump a peritoneal fluid mixture from the peritoneal cavity through the drainage conduit into the bladder through the exit conduit, and
    wherein the peritoneal fluid mixture comprises the infusate comprising the osmotic agent.

2. The system of claim 1, further comprising an implantable controller associated with the implantable pump.

3. The system of claim 2, wherein the implantable controller is configured to monitor a physiologic parameter, the implantable controller programmed to cause the implantable pump to pump the peritoneal fluid mixture from the peritoneal cavity to the bladder responsive to a value of the monitored physiologic parameter.

4. The system of claim 3, wherein the monitored physiological parameter comprises pressure, pH, temperature, electrolyte concentration, analyte concentration, or any combination thereof of the peritoneal cavity or the bladder or both.

5. The system of claim 2, wherein the implantable controller is configured to monitor a difference in pressure between the peritoneal cavity and the bladder.

6. The system of claim 1, further comprising a reservoir adapted for coupling to the implantable pump via the reservoir conduit,
    wherein the implantable pump is configured to pump the infusate comprising the osmotic agent from the reservoir through the reservoir conduit into the peritoneal cavity through the drainage conduit to form the peritoneal fluid mixture in the peritoneal cavity.

7. The system of claim 6, further comprising an implantable controller associated with the implantable pump, the implantable controller configured to monitor a physiologic parameter, the implantable controller programmed to cause the implantable pump to pump the infusate from the reservoir to the peritoneal cavity responsive to a value of the monitored physiologic parameter.

8. The system of claim 7, wherein the monitored physiological parameter comprises pressure, pH, temperature, electrolyte concentration, analyte concentration, or any combination thereof of the peritoneal cavity or the bladder or both.

9. The system of claim 6, wherein the implantable pump is configured to pump the infusate comprising the osmotic agent from the reservoir through the reservoir conduit into the peritoneal cavity through the drainage conduit as a function of time.

10. The system of claim 6, wherein the reservoir is adapted for implantation.

11. The system of claim 1, wherein the implantable pump is configured to pump the peritoneal fluid mixture from the peritoneal cavity through the drainage conduit into the bladder through the exit conduit as a function of time.

12. The system of claim 1, further comprising an inductive recharging circuit for recharging the internal battery.

13. The system of claim 1, wherein the drainage conduit comprises a semi-permeable conduit.

\* \* \* \* \*